US009145447B2

(12) United States Patent
Wang et al.

(10) Patent No.: US 9,145,447 B2
(45) Date of Patent: Sep. 29, 2015

(54) PHOTOCONVERTIBLE FLUORESCENT PROTEINS

(75) Inventors: Jiwu Wang, La Jolla, CA (US); Robert Earl Campbell, Edmonton (CA); Hiofan Hoi, Edmonton (CA); Nathan Christopher Shaner, Seaside, CA (US)

(73) Assignees: Allele Biotechnology & Pharmaceuticals, Inc., San Diego, CA (US); University of Alberta, TEC Edmonton, Edmonton (CA)

( * ) Notice: Subject to any disclaimer, the term of this patent is extended or adjusted under 35 U.S.C. 154(b) by 306 days.

(21) Appl. No.: 12/960,397

(22) Filed: Dec. 3, 2010

(65) Prior Publication Data
US 2011/0214192 A1 Sep. 1, 2011

Related U.S. Application Data

(60) Provisional application No. 61/266,912, filed on Dec. 4, 2009.

(51) Int. Cl.
C12N 5/14 (2006.01)
C12N 5/16 (2006.01)
C07K 14/435 (2006.01)

(52) U.S. Cl.
CPC .............................. *C07K 14/43595* (2013.01)

(58) Field of Classification Search
CPC ...... C07K 14/43595; C12N 5/14; C12N 5/16; A01K 67/0275
USPC ............................................. 530/802; 800/13
See application file for complete search history.

(56) References Cited

U.S. PATENT DOCUMENTS

| 6,800,733 B2 | 10/2004 | Tsien |
| 7,166,444 B2 | 1/2007 | Lukyanov et al. |
| 2009/0191622 A1* | 7/2009 | Almond et al. ............. 435/320.1 |
| 2010/0168396 A1* | 7/2010 | Mushegian et al. ........ 530/387.9 |

OTHER PUBLICATIONS

Adam et al. "Structural basis of enhanced photoconversion yield in green fluorescent protein-like protein Dendra2." *Biochemistry* 2009, 48:4905-4915.
Ai et al. "Directed evolution of a monomeric, bright and photostable version of *Clavularia* cyan fluorescent protein: structural characterization and applications in fluorescence imaging." *The Biochemical Journal* 2006, 400:531-540.
Ando et al. "An optical marker based on the UV-induced green-to-red photoconversion of a fluorescent protein." *Proc Natl Acad Sci U S A* 2002, 99:12651-12656.
Brannon and Magde. "Absolute Quantum Yield Determination by Thermal Blooming—Fluorescein." *J Phys Chem* 1978, 82:705-709.
Campbell et al. "A monomeric red fluorescent protein." *Proc Natl Acad Sci U S A* 2002, 99:7877-7882.

Chattoraj et al. "Ultra-fast excited state dynamics in green fluorescent protein: multiple states and proton transfer," *Proc Natl Acad Sci U S A* 1996, 93:8362-8367.
Chudakov et al. "Tracking intracellular protein movements using photoswitchable fluorescent proteins PS-CFP2 and Dendra2." *Nature protocols* 2007, 2:2024-2032 Abstract Only.
Fischer and Georges. "Fluorescence quantum yield of Rhodamine 6G in ethanol as a function of concentration using thermal lens spectrometry." *Fluorescence quantum yield of Rhodamine 6G in ethanol as a function of concentration using thermal lens spectrometry* 1996, 260:115-118.
Gurskaya et al. "Engineering of a monomeric green-to-red photoactivatable fluorescent protein induced by blue light." *Nature Biotechnology* 2006, 24:461-465.
Habuchi et al. "mKikGR, a monomeric photoswitchable fluorescent protein." *PloS One* 2008, 3:e3944.
Hayashi et al. "Crystallographic Evidence for Water-assisted Photo-induced Peptide Cleavage in the Stony Coral Fluorescent Protein Kaede." J. Mol. Biol., 2007, 372:918-926.
Kremers et al. "Photoconversion in orange and red fluorescent proteins." *Nature Methods* 2009, 6:355-358.
McKinney et al. "A bright and photostable photoconvertible fluorescent protein." *Nature Methods* 2009, 6:131-133.
Mizuno et al. "Photo-induced peptide cleavage in the green-to-red conversion of a fluorescent protein." *Molecular Cell* 2003, 12: 1051-1058.
Nienhaus et al. "Photoconvertible fluorescent protein EosFP: biophysical properties and cell biology applications." *Photochemistry and Photobiology* 2006, 82:351-358.
Ormo et al. "Crystal structure of the *Aequorea victoria* green fluorescent protein." *Science* 1996, 273:1392-1395, New York, NY.
Shaner et al. "Improved monomeric red, orange and yellow fluorescent proteins derived from *Discosoma* sp. red fluorescent protein." *Nature Biotechnology* 2004, 22:1567-1572.
Tsutsui et al. "Semi-rational engineering of a coral fluorescent protein into an efficient highlighter." *EMBO Reports* 2005, 6:233-238.
Tsutsui et al. "The E1 mechanism in photo-induced beta-elimination reactions for green-to-red conversion of fluorescent proteins." *Chemistry & Biology* 2009, 16:1140-1147.
Ward, W.W. "Biochemical and physical properties of GFP" *Green Fluorescent Protein: Properties, Applications, and Protocols* 1998, (New York, Wiley).
Wiedenmann et al. "EosFP, a fluorescent marker protein with UV-inducible green-to-red fluorescence conversion." *Proc Natl Acad Sci U S A* 2004, 101:15905-15910.

* cited by examiner

Primary Examiner — Kevin Hill
(74) Attorney, Agent, or Firm — Duane Morris LLP

(57) ABSTRACT

The present disclosure provides an isolated nucleic acid sequence encoding a monomeric photoconvertible fluorescent protein, and fragments and derivatives thereof. Also provided is a method for engineering the nucleic acid sequence, a vector comprising the nucleic acid sequence, a host cell comprising the vector, and use of the vector in a method for expressing the nucleic acid sequence. The present disclosure further provides an isolated nucleic acid, or mimetic or complement thereof, that hybridizes under stringent conditions to the nucleic acid sequence. Additionally, the present provides a monomeric photoconvertible fluorescent protein encoded by the nucleic acid sequence, as well as derivatives, fragments, and homologues thereof. Also provided is an antibody that specifically binds to the photoconvertible fluorescent protein.

21 Claims, 12 Drawing Sheets

FIG. 2

(mTFP1= SEQ ID No. 3), (mClavGR 1.0= SEQ ID No. 4), (mClavGR 1.1= SEQ ID No. 5), (mClavGR 2.0= SEQ ID No. 2), (mEos2= SEQ ID No. 6), (Dendra2= SEQ ID No. 7), (Kaede= SEQ ID No. 8), (mKikGR= SEQ ID No. 9)

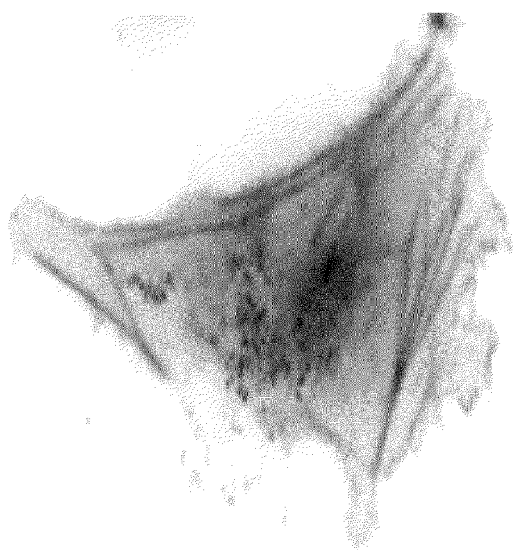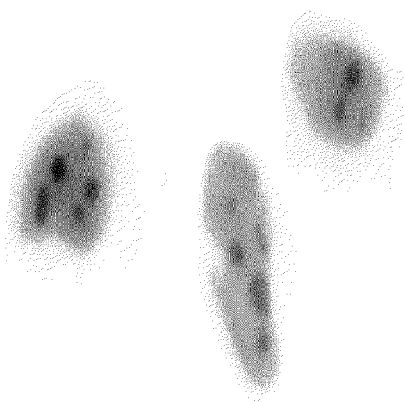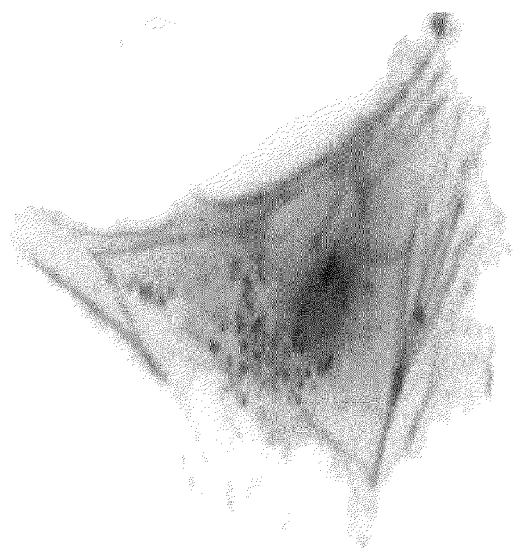
FIG. 7A			FIG. 7B

SEQ ID NO: 1 (DNA sequence of mClavGR2)
Atggtgagcaagggcgaggagaccatcatgagcgtgatcaagcctgacatgaagatcaagctgcgcatggagggcaac
gtgaacggccacgccttcgtgatcgagggcgagggcagcggcaagcccttcgagggcatccagacgattgatttggag
gtgaaggagggcgccccgctgcccttcgcctacgacatcctgaccaccgccttccactacggcaaccgcgtgttcacc
aagtaccccgaggacatccctgactacttcaagcagagcttccccgagggctacagctgggagcgcagcatgacctac
gaggacggcggcatctgcatcgccaccaacgacatcacgatggaggaggacagcttcatcaacaagatccacttcaag
ggcacgaacttcccccccaacggcccgtgatgcagaagaggaccgtgggctgggaggccagcaccgagaagatgtac
gtgcgcgacggcgtgctgaagggcgacgtgaagatgaagctgctgctgaagggcggcggccactaccgctgcgacttc
cgcaccacctacaaggtcaagcagaaggccgtaaagctgcccgactaccacttcgtggaccaccgcatcgagatcctg
agccacgacaaggactacaacaaggtgaagctgtacgagcacgccgtggcccacagcggcctgcccggcatggacgag
ctgtacaagtaa SEQ ID NO: 2 (Polypeptide sequence of mCalvGR2)
M V S K G E E T I M S V I K P D M K I K L R M E G N V N G H A F V I E
G E G S G K P F E G I Q T I D L E V K E G A P L P F A Y D I L T T A F H
Y G N R V F T K Y P E D I P D Y F K Q S F P E G Y S W E R S M T Y E
D G G I C I A T N D I T M E E D S F I N K I H F K G T N F P P N G P V M
Q K R T V G W E A S T E K M Y V R D G V L K G D V K M K L L L K G G
G H Y R C D F R T T Y K V K Q K A V K L P D Y H F V D H R I E I L S H
D K D Y N K V K L Y E H A V A H S G L P G M D E L Y K

FIG. 11

| Template | | Notes |
|---|---|---|
| dClavGR1.6 | 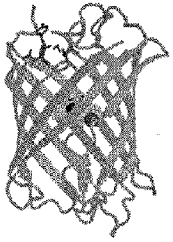 | A cluster of residues located near the 'top' of the central helix. Substitution of residue 74 previously shown to benefit KikGR {Tsutsui 2005}. |
| dClavGR1.6 |  | Adjacent to H197, which is in close proximity to the chromophore. Substitution of residue 198 previously shown to benefit KikGR {Tsutsui 2005}. |
| dClavGR1.6 |  | Adjacent to M163, which is in close proximity to the chromophore. K162A similar with K162K. |
| dClavGR1.6 |  | Interacts with phenolate of chromophore. M163K brighter in green state but did not photoconvert to the red state. |
| mClavGR1 |  | Close proximity to chromophore. Substitutions at residues 44 and 199 previously shown to benefit KikGR {Tsutsui 2005}. |
| mClavGR1 |  | Previously reported {Adam 2009} to influence $pK_a$ of related FPs. |
| mClavGR1.8 |  | Disrupted residual dimerization tendency |
| mClavGR2 |  | K125N similar to K125K |

FIG. 12

PHOTOCONVERTIBLE FLUORESCENT PROTEINS

CROSS REFERENCE TO RELATED APPLICATIONS

The present application claims priority from U.S. Provisional Patent Application No. 61/266,912 filed on Dec. 4, 2009, which is incorporated herein in its entirety by reference.

FIELD OF THE INVENTION

The present invention relates to fluorescent proteins and, in particular, photoconvertible fluorescent proteins.

BACKGROUND

In recent years a handful of Aequorea green FP (GFP) homologues cloned from Anthozoan organisms have been reported to undergo irreversible photoconversion from a green fluorescent to a red fluorescent species upon illumination with light of approximately 400 nm. To date, the naturally occurring photoconvertible proteins that have received the most attention are Kaede from coral *Trachyphyllia geoffroyi* (Ando et al., 2002), EosFP from stony coral *Lobophyllia hemprichii* (Wiedenmann et al., 2004), and Dendra from octocoral *Dendronephthya* sp. (Gurskaya et al., 2006). It has also been demonstrated that a non-photoconvertible FP can be engineered to be photoconvertible FPs. Specifically, the photoconvertible FP known as KikGR was engineered from the green fluorescent KikG of the coral *Favia favus* (Tsutsui et al., 2005).

All green-to-red photoconvertible FPs characterized to date share a common His-Tyr-Gly-derived chromophore structure, and a common photoconversion mechanism (FIG. 1) (Mizuno et al., 2003). The newly synthesized protein first folds into the characteristic beta-barrel structure that defines the Aequorea GFP superfamily (Ormo et al., 1996), and undergoes the steps of post-translational modification that lead to the formation of a green fluorescent chromophore with a conjugated system identical to that of the Aequorea GFP chromophore. The chromophore can exist in either its neutral phenol form or the anionic phenolate form (FIG. 1). Exactly where the equilibrium between these two forms lies is dependent on the local microenvironment of the chromophore (as determined by the amino acid substitutions in close proximity to it) and the pH of the solution. The green-to-red photoconvertible FPs are distinguished from their non-photoconvertible brethren, by the respective consequences of exciting the neutral form which absorbs most strongly at ~400 nm. In wild-type Aequorea GFP the excited state of the neutral form undergoes excited state proton transfer to form the anionic form, which then emits green fluorescence (Chattoraj et al., 1996). An Aequorea GFP variant that does fluoresce from the neutral form of the excited state has been engineered (Tsutsui et al., 2009). In the case of the green-to-red photoconvertible FPs, excitation of the neutral form leads to a break of the polypeptide chain through the effective beta-elimination of the residue that immediately precedes the chromophore-forming His-Tyr-Gly tripeptide (Mizuno et al., 2003; Tsutsui et al., 2009). This elimination reaction results in the installation of a new double bond between C-alpha and C-beta of the His residue, placing the side chain imidazole into conjugation with the remainder of the avGFP-type chromophore. This extended conjugation decreases the HOMO-LUMO gap and thus shifts the emission into the orange-to-red region of the visible spectrum. Photoconversion via alternate mechanisms has been observed in other color classes of FP (Chudakov et al., 2004; Kremers et al., 2009).

Kaede, the first example of a FP that can undergo an irreversible green-to-red photoconversion upon illumination with UV light, was initially described by Miyawaki and coworkers in 2002 (Ando et al., 2002). Unfortunately, the range of potential applications for Kaede remains limited by the fact that it is an obligate tetramer (Hayashi et al., 2007), and no monomeric variants have been reported. Unlike monomeric FPs, tetrameric FPs are generally detrimental to the proper trafficking and localization of recombinant fusion proteins (Campbell et al., 2002). To produce a monomeric green-to-red photoconvertible FP, the same workers appear to have had more success with engineered variants of the tetrameric KikGR FP which is substantially brighter and more efficiently photoconverted than Kaede (Tsutsui et al., 2005). A monomeric version of KikGR, known as mKikGR, has recently been reported (Habuchi et al., 2008).

The two other green-to-red photoconvertible FPs, EosFP and Dendra (Gurskaya et al., 2006; Wiedenmann et al., 2004), have both been subjected to protein engineering to convert the wild-type tetramers into monomers (Adam et al., 2009; McKinney et al., 2009). However, it is apparent that in both cases the 'monomeric' FP does retain some tendency to form dimers at high concentrations (McKinney et al., 2009). The monomeric variant of EosFP, known as mEos, was created through the introduction of 2 point mutations that disrupted the protein-protein interfaces of the tetrameric species (Nienhaus et al., 2005; Wiedenmann et al., 2004). Expression of mEos temperatures of less than 30 degrees C. is problematic (Wiedenmann et al., 2004), but an effectively monomeric tandem dimer variant does express well at 37 degrees C. (Nienhaus et al., 2006). The problem of poor expression of mEos at 37 degrees C. has been overcome with the engineering of mEos2 (McKinney et al., 2009) through the targeted substitution of residues with solvent exposed side chains. Although mEos2 has been reported to retain some propensity for dimer formation, this property does not appear to have adverse effects on the subcellular targeting of a variety of fusion proteins (McKinney et al., 2009).

As with mEos, Dendra is a monomeric green-to-red photoconvertible FP derived from the wild-type tetrameric DendGFP (Gurskaya et al., 2006). Further optimization of Dendra produced the Dendra2 variant, which is claimed to be brighter and faster maturing (Chudakov et al., 2004). Unlike other members of the class of green-to-red photoconvertible FPs that require UV illumination to promote photoconversion, Dendra can be converted to its red fluorescent state by either cyan or UV wavelengths of light. Although Dendra2 generally behaves as a monomer in relatively dilute solutions, it was observed to reconstitute a protein-protein interface very similar to the typical AC dimer interface observed in crystal structures of tetrameric FPs (Adam et al., 2009). It has been reported that Dendra2 can fluoresce from either the neutral or anionic forms of the photoconverted species.

SUMMARY OF THE INVENTION

In view of the problems associated with known photoconvertible fluorescent proteins, as described above, the inventors have engineered a series of novel non-oligomerizing photoconvertible FPs with surprising and unexpected favorable properties by designing and screening. One of the exemplary compositions was designated monomeric Clavularia-derived green-to-red photoconvertible 2 (mClavGR2) SEQ ID NO: 1. The designation "Clavularia-derived" does not imply that the novel proteins are significantly similar to Clavularia fluorescent proteins in any way beyond the fact that Clavularia FP derivatives were used as references and mTFP1 as a "template" during the design.

Accordingly, in one aspect, the present invention comprises an isolated nucleic acid sequence encoding a non-oligomerizing photoconvertible FP. In certain embodiments, the nucleic acid sequence may be compatible with mammalian (e.g., human) or other species' codon usage.

In another embodiment, the nucleic acid sequence encodes a polypeptide sequence that has at least about 95% homology with the polypeptide encoded by SEQ ID NO: 2.

In yet another embodiment, a nucleic acid present in other than its natural environment, wherein said nucleic acid encodes a green-to-red chromoprotein or fluorescent mutant thereof, and wherein said nucleic acid has a sequence identity of at least about 90% with SEQ ID NO: 1.

In still another aspect, the present disclosure provides a vector that includes a nucleic acid sequence encoding a non-oligomerizing photoconvertible FP. In one embodiment, the vector is a plasmid, a viral vector, or a linear form of DNA template.

In another embodiment, the nucleic acid sequence of the vector is cDNA. Also provided is a host cell comprising the vector.

The present invention further provides use of the vector in a method for expressing the nucleic acid sequence in mammalian cells, plant cells, yeast cells, bacterial cells, etc. In one embodiment, the nucleic acid sequence is expressed as a tandem genetic fusion to another protein.

In one embodiment, the novel protein may be a monomer or dimer. In one embodiment, the chromophore comprises the amino acid sequence tyrosine-glycine (YG). For example, the chromophore may comprise the amino acid sequence His-Tyr-Gly.

In one embodiment, the *Clavularia* TFP variant may be a monomer or dimer. In one embodiment, the chromophore comprises the amino acid sequence tyrosine-glycine (YG). For example, the chromophore may comprise the amino acid sequence glutamine-tyrosine-glycine (QYG); the chromophore may also comprise the amino acid sequence alanine-tyrosine-glycine (AYG), cysteine-tyrosine-glycine (CYG), glycine-tyrosine-glycine (GYG) or serine-tyrosine-glycine (SYG).

In another embodiment, the fluorescent protein comprises at least one or more of the mutations as listed in Table 2 corresponding to mClavGR1, mClavGR1.1, mClavGR2.0. In a further embodiment, the photoconvertible FP comprises at least one or more of the following mutations T6bI, T41I, D77E, F99Y, K115E, E127T, K139R, A183V, H220R, S221N, G222S, L223T, P224D (dCalvGR1.6, mClavGR1.8, mClavGR2.0) as in FIG. 3.

In yet another aspect, the present invention provides an antibody that specifically binds to the FPs of the invention. In one embodiment, the antibody is a polyclonal antibody; in another embodiment, the antibody is a monoclonal antibody.

In one aspect, a transgenic animal is provided comprising the nucleic acid having a sequence identity of at least about 90% with SEQ ID NO: 1.

In one aspect, a transgenic plant is provided comprising the nucleic acid having a sequence identity of at least about 90% with SEQ ID NO: 1.

Additional variations, aspects and advantages of the present invention will be apparent in view of the following descriptions. It should be understood, however, that the detailed description and the specific examples, while indicating preferred embodiments of the invention, are given for the purpose of illustration only, since various changes and modifications within the spirit and scope of the invention will become apparent to those skilled in the art from these detailed depictions and descriptions.

BRIEF DESCRIPTION OF THE DRAWING

The invention will now be described in relation to the drawings in which:

FIG. 2. Sequence alignment of mClavGR variants and closely related proteins relevant to this study. Substitutions in mClavGR1, relative to mTFP1, are represented as black text on a gray background. Substitutions in later mClavGR variants that were identified during the directed evolution are shown as white text on a black background. Residues with side chains directed towards the interior of the beta-barrel are enclosed in black boxes. The chromophore forming residues are 66-68 in this alignment.

FIGS. 7A and 7B. (A) mClavGR2-β-actin and (B) mClavGR2-NLS expressed in Hela cells. The top images are before photoconvertion and the bottoms are after photoconversion. In (B), only nucleus 1 is selectively photoconverted into red.

FIG. 11. Nucleic acid and amino acid sequences of mClavGR2

FIG. 12. PDB generated figures corresponding to Table 1.

DETAILED DESCRIPTION

Figure 1:
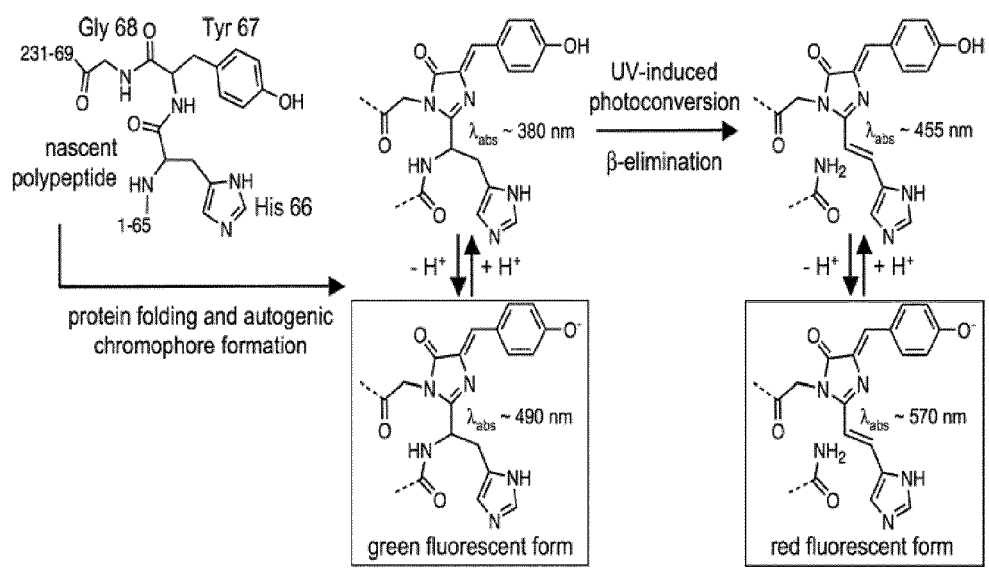
FIG. 1. Chromophore structure and UV-induced modifications of green-to-red photoconvertible FPs (Mizuno et al., 2003). Residue numbers for the nascent polypeptide are for the mTFP1-derived variants described in this work. Dashed lines represent connections to the polypeptide chain of the protein.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

The growing number of reports on optimized photoconvertible FPs reflects the growing demands on these proteins with respect to their enabling role in some popular cell biology applications. In particular, there is a need for bright and monomeric photoconvertible proteins, since these tools can enable the highest-precision super-resolution fluorescence imaging.

In an effort to create a new monomeric photoconvertible FP with favorable properties, we embarked on a strategy distinct from that previously employed. Rather than starting with a tetrameric photoconvertible protein and engineer it to be monomeric, we sought to start with a well-characterized monomeric coral-derived FP and engineer it to be a green-to-red photoconvertible FR Our starting template is a monomeric version of *Clavularia* sp. cyan FP (cFP484, a wild-type Clavularia cyan FP) known as mTFP1 (monomeric teal FP 1) (Ai et al., 2006).

In an effort to mitigate some of the difficulties of the prior art, we embarked on a strategy to create a monomeric photoconvertible FP this is distinctly different from that previously employed. The unpredictable nature of FP generation by mutagenesis is well understood by those skilled in the art, In many instances, modifications of particular locations in the polypeptide sequence may have no effect upon the properties of the resultant polypeptide (e.g. U.S. Pat. Nos. 6,800,733; 7,166,444). The FPs of the instant disclosure contain specific mutations which resulted in unexpected and surprising favorable properties.

The use of green-to-red photoconvertible fluorescent proteins (FPs) enables researchers to selectively highlight a subcellular population of a fusion protein of interest and image its dynamics in vivo. In an effort to create previously unknown and unavailable photoconvertible FPs with properties that could overcome the limitations imposed by the oligomeric structure of the natural photoconvertible FPs, we set out to design a new monomeric photoconvertible FP. Using monomeric versions of *Clavularia* sp. cyan FP and a number of other fluorescent proteins as references, we used sequence-alignment-guided design in order to engineer a novel chromophore environment that could support photoconversion. The designed gene was synthesized and, when expressed in *E. coli*, was found to produce green fluorescent colonies that gradually switched to red after exposure to sunlight for 1-2 hours. We subjected this first-generation FP (named ClavGR1) to a combination of random and targeted mutagenesis and screened libraries for efficient photoconversion using a custom-built 'photoconversion chamber' in which a 10 cm Petri dish is evenly illuminated with light from 594 individual 405 nm LEDs. Following more than 15 rounds of library creation and screening, we settled on an optimized version, known as mClavGR2, that has 8 mutations relative to mClavGR1. Key improvements of mClavGR2 relative to mClavGR1 include a 1.2-fold brighter red species, two-fold higher photoconversion efficiency, and dramatically improved chromophore maturation in *E. coli*. The monomeric status of mClavGR2 has been demonstrated by gel-filtration chromatography, as well as the functional expression of a mClavGR2-β-actin fusion in mammalian cells.

In one example, all of the known photoconvertible fluorescent proteins, including EosFP, Dendra2, KikGR and Kaede, were aligned to find the consensus at each amino acid position. Amino acids of >50% consensus were chosen for the mClavGR 1 protein. At positions with no clear consensus, the corresponding residue in mTFP1 (Ai et al., 2006) was used. Residues of mTFP1 that had been substituted during the conversion of the wild type cFP484 tetramer into a monomer were maintained in the design of the consensus protein. The designed gene was synthesized and when expressed in *E. coli*, was found to exhibit green fluorescence that gradually switched to red after exposure to sunlight for 1-2 hours.

In another example, in order to direct the evolution of mClavGR1 towards variants that were brighter and exhibited more efficient photoconversion, we developed a method for photoconverting fluorescent proteins when expressed in colonies of *E. coli*. Our method involves a 3-step process. In the first step, two images of the colonies grown on a Petri dish are acquired; one image of the green fluorescence and one image of the red fluorescence. In the second step, the plate is placed in a 'photoconversion chamber' where it is evenly illuminated with the light from six 9×11 arrays of 405 nm light emitting diodes (LEDs) (OptoDiode Corporation, Newbury Park, Calif.). Following 10 to 20 min of illumination, the plate is imaged again using the same filters that were used in the first step. The digital images are loaded into Image Pro plus where they are aligned and processed using a custom macro. The output of the macro is a list of the mean intensity for each colony in each of the 4 images. This data is plotted as 'green fluorescence before photoconversion' vs. 'red fluorescence after photoconversion'. Colonies that exhibited the highest intensities in both channels were picked and used as the template for the following round of library creation. In most cases, approximately 5 to 15 of the brightest variants out of 4,000-8,000 were picked in each round.

Figure 3:
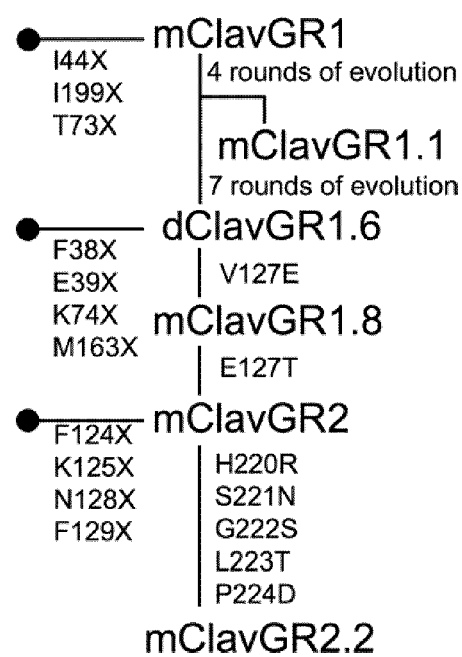
FIG. 3. A genealogy of ClavGR variants. The lines ending in a filled circle indicate site-directed libraries that were created and screened, but did not produce improved variants. An 'X' represents a selection of amino acids as specified in Table 1.
Figure 4A:
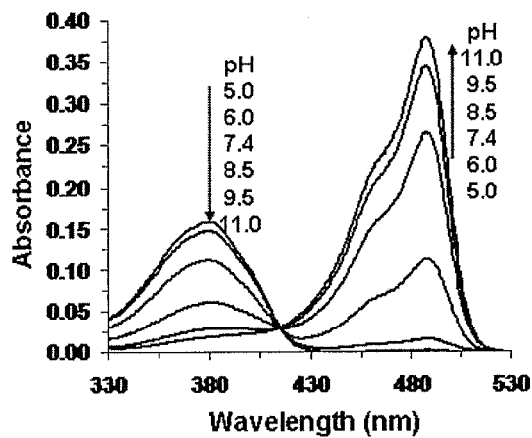
FIGS. 4A thru 4D. Absorption spectra of (A) green and (C) red mClavGR2, recorded from pH 5 to pH 11. Arrow indicates change of pH. (B and D) pH dependence of fluorescence. The line represents the best fit of the data using the Henderson-Hasselbalch equation.
Figure 4B:
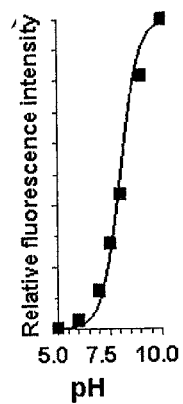
Figure 4C:
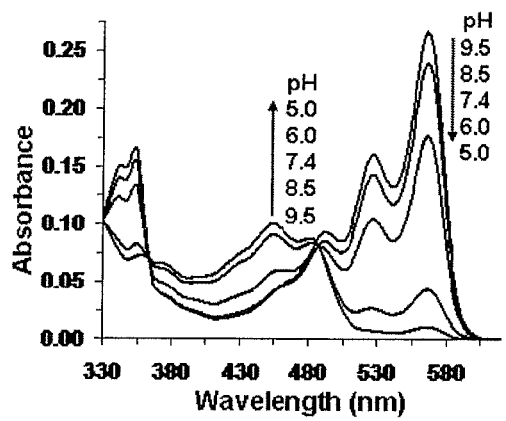
Figure 4D:
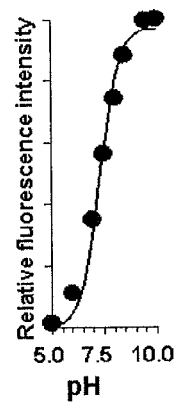

Starting from mClavGR1, 11 rounds of library creation and screening were undertaken. Following 4 rounds of screening for high brightness before and after photoconversion, we sequenced the clone with the highest fluorescence intensity in both the green (before photoconversion) and red (after photoconversion) channels. This clone, designated mClavGR1.1, was equivalent to mClavGR1+T6bI, S34R, K36R, K74R, M113I, L166Q, Y173H (FIG. 2). Error prone PCR and StEP shuffling (32) with a template mixture of mClavGR1.1 and other bright variants from each round was performed for 7 more rounds. During these additional rounds we picked colonies that exhibited either the highest brightness or the highest ratio of red fluorescence after to green fluorescence before photoconversion. While we primarily relied on the diversity generated by error prone PCR and StEP shuffling, we also targeted a number of specific positions that have previously been shown to be important for the properties of homologous fluorescent proteins (Table 1). These rationally generated libraries were screened in a manner identical to that used for the random libraries. The brightest variant after the 11th round of directed evolution was designated as mClavGR1.6, which was equivalent to mClavGR1+T6bI, T41I, D77E, F99Y, K115E, E127V, K139R, A183V. Characterization of the oligomeric state of 'mClavGR1.6' by gel filtration chromatography revealed that the protein existed as a dimer. So, we rename mClavGR1.6 as dClavGR1.6 (d prefix indicates a dimer). dClavGR1.6 is about 5-fold brighter than mClavGR1 in *E. coli* and shares only the T6bI substitution with mClavGR1.1. Analysis of the substitutions present in dClavGR1.6 suggested that the E127V substitution, which is located at a dimeric interface, was most likely key in reconstituting the dimer interface. In order to get rid of the dimerize propensity accidentally introduced by E127V during random mutation, we reverse Val127 back into glutamate acid through site directed mutation. However, mClavGR1.8, which is equal to dClavGR1.6+V127E, was only half as bright when expressed in *E. coli*. We then tried the V127T mutation that improves the monomerization of mEosFP and Dendra2, and found out mClavGR2, which equals mClavGR1+T6bI, T41I, D77E, F99Y, K115E, E127T, K139R, A183V, matures faster than mClavGR1.8 in *E. coli*. A genealogy of all mClavGR variants is provided in FIG. 3 and all variants are explicitly defined in Table 2.

Although the improved variants are substantially brighter than mClavGR1 when expressed in *E. coli*, their inherent brightness (i.e., the product of ε and Φ) has improved only modestly (Table 3). This indicates that the improvement of brightness seen in *E. coli* is very likely due to more complete maturation or more efficient folding of the fluorescent protein. Although mClavGR1.1 matures more thoroughly in *E. coli*, its photoconversion efficiency is substantially lower as judged by the relative photoconversion quantum yield and relative photoconversion efficiency (Table 3). Thus, as a result of compromise between maturation and photoconversion efficiency, mClavGR2 was selected for further study.

TABLE 1

Positions targeted for partial or complete randomization by mutagenesis. Figures were generated from PDB ID 2HQK (Ai et al., 2006) using MacPyMol (DeLano Scientific). Residues being substituted are indicated in red* (all color descriptions are represented on black and white scale.

| Template | Residue(s) | Substitution(s) | Codon(s) | Result |
| --- | --- | --- | --- | --- |
| dClavGR1.6 | F38 | All 20 amino acids | NNK | no improved variants |
|  | E39 | Asp, Glu, Gly, His, Lys, Asn, Gln, Arg, Ser | VRN |  |
|  | K74 | Asp, Glu, Gly, His, Lys, Asn, Gln, Arg, Ser | VRN |  |
| dClavGR1.6 | R198 | Ala, Gly, Leu, Met, Arg, Ser, Thr, Val, Trp | DBG | identified R198A |
| dClavGR1.6 | K162 | All 20 amino acids | NNK | no improved variants |
| dClavGR1.6 | M163 | His or all 20 amino acids | CAY or NNK | no improved variants |
| mClavGR1 | I44 | All 20 amino acids | NNK | no improved variants |
|  | I199 | Leu, Ile, Met, Val, His, Gln, Asn, Lys Asp, Glu | VWK |  |
| mClavGR1 | T73 | All 20 amino acids | NNK | no improved variants |
| mClavGR1.8 | E127 | Thr | ACG | identified E127T |
| mClavGR2 | F124 | Phe, Ile, Leu, Val | NTT | no improved variants |
|  | K125 | His, Lys, Gln, Asn | AAM, MAG |  |
|  | N128 | Pro, Arg, Ser, Thr | MSC |  |
|  | F129 | Phe, Ile, Leu, Val | NTT |  |

TABLE 2

Definitions of variants described in this work.

| Protein variant | Substitutions and modifications relative to parent |
| --- | --- |
| mTFP1[a] = | cFP484[b] + delete all residues before 6a and add MVSKGEE (SEQ ID NO: 10), H42N, L44I, S62T, N63T, Q66A, L72F, A80P, D81N, R123H, F124L, D125K, M127E, L141T, K142G, E144D, P145A, I149R, V158K, I161V, S162K, S164K, Y173H, C175V, S179T, K182R, V186A, L213V, N216S, Y221N, L223T, L224D, delete all residues after 224 and add GMDELYK (SEQ ID NO: 11). |
| mClavGR1[c] = | mTFP1 + G6dS, K17R, E34S, Y38F, D39E, N42Q, N45D, S57A, A66H, A71V, N81D, T96S, K102G, V105C, K106I, V107A, K108T, S109N, S112T, E115K, Y120N, E121K, L124F, D144E, R149K, H163M, E168K, H173Y, V175C, K178R, I180T, R182K, Q184a insertion, N203S, T212K, V213L, S216H, R220H, N221S, S222G, T223L, D224P |
| mClavGR1.1 = | mClavGR1 + T6bI, S34R, K36R, K74R, M113I, L166Q, Y173H |
| dClavGR1.6 = | mClavGR1 + T6bI, T41I, D77E, F99Y, K115E, E127V, K139R, A183V |
| mClavGR1.8 = | mClavGR1 + T6bI, T41I, D77E, F99Y, K115E, K139R, A183V |
| mClavGR2 = | mClavGR1 + T6bI, T41I, D77E, F99Y, K115E, E127T, K139R A183V |

[a]Previously described.
[b]cFP484 is the wild-type protein from *Clavularia* (Genbank accession AAF03374) (4).
[c]The key monomerizing mutations R123H, D125K, and M127E (of the A-B interface) and S162K and S164K (of the AC interface) of mTFP1 have been retained in mClavGR1.

TABLE 3

Properties of mClavGR1 and its improved variants

| protein | | $\lambda_{ab}$ (nm) | $\lambda_{em}$ (nm) | $\epsilon^a$ | $\Phi$ | brightness[b] | $pK_a$ | $\Phi_{PC,GRX}/\Phi_{PC,GR1}{}^c$ | $E_{PC,GRX}/E_{PC,GR1}{}^d$ |
| --- | --- | --- | --- | --- | --- | --- | --- | --- | --- |
| mClavGR1 | green | 486 | 503 | 16 | 0.84 | 14 | 8.0 | 1.0 | 1.0 |
|  | red | 565 | 582 | 21 | 0.56 | 12 | 7.4 |  |  |
| mClavGR1.1 | green | 487 | 504 | 18 | 0.83 | 15 | 7.9 | 0.8 | 1.0 |
|  | red | 565 | 582 | 25 | 0.58 | 14 | 7.3 |  |  |

TABLE 3-continued

Properties of mClavGR1 and its improved variants

| protein | | $\lambda_{ab}$ (nm) | $\lambda_{em}$ (nm) | $\epsilon^a$ | $\Phi$ | brightness[b] | $pK_a$ | $\sqrt{\Phi_{PC,GRX}}/\sqrt{\Phi_{PC,GR1}}$[c] | $E_{PC,GRX}/E_{PC,GR1}$[d] |
|---|---|---|---|---|---|---|---|---|---|
| mClavGR2 | green | 488 | 504 | 19 | 0.77 | 15 | 8.0 | 1.2 | 1.8 |
| | red | 566 | 583 | 32 | 0.53 | 17 | 7.3 | | |

[a] Unit of $mM^{-1} cm^{-1}$.
[b] Product of $\epsilon$ and $\Phi$ in $mM^{-1} cm^{-1}$. For comparison, the brightness of mCherry is 16 $mM^{-1} cm^{-1}$ and the brightness of EGFP is 34 $mM^{-1} cm^{-1}$ (1).
[c] Photoconversion quantum yield relative to mClavGR1.
[d] Photoconversion contrast relative to mClavGR1.

Figure 5:
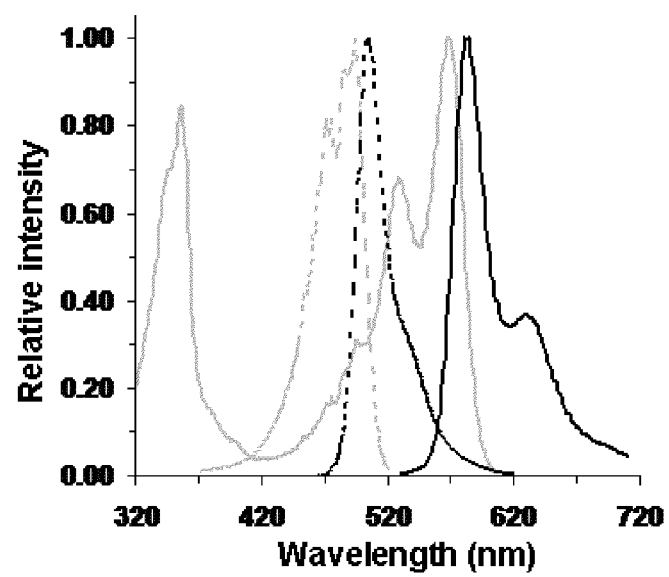
FIG. 5. Excitation (grey) and emission (black) spectra of both green form (dash) and red form (solid) of mClavGR2.
Figure 9:
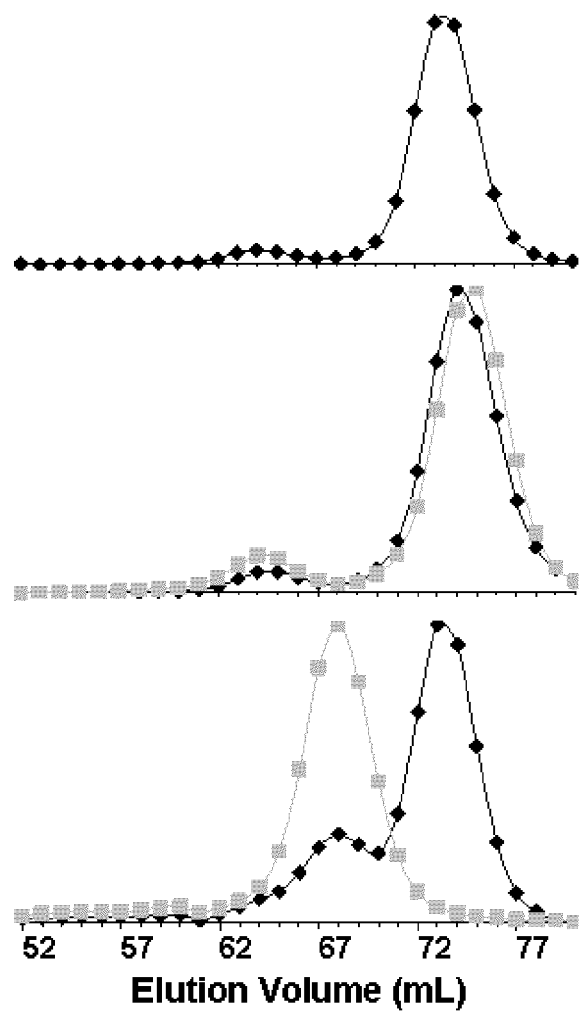
FIG. 9. Characterization of oligomeric structure. Upper trace is mClavGR2 alone. Middle trace is a coinjection of mCherry (grey) and mClavGR2 (black) with wavelength-specific detection. The lower trace is a coinjection of dTomato (grey) and mClavGR2 (black) with wavelength-specific detection.

The pH-dependent absorption spectra of the green and red forms of mClavGR2 are shown in FIG. 4. The two peak at 380 nm and 488 nm corresponding to the neutral (phenol) and anionic (phenolate) forms of the green chromophore. Only the anionic form is green fluorescent before photoconversion since only the 488 nm peak is in the excitation spectrum (FIG. 5). However, it's the neutral form that is reported to be responsible for the photoconversion, as is evident from action spectra of Kaede (Ando et al., 2002), EosFP (Wiedenmann et al., 2004) and Dendra2 (Gurskaya et al., 2006). This is also supported by the result of our rational libraries. In order to improve the pKa of mClavGR2, we generated the mClavGR2/Met163His mutant and found out that this mutant has very poor photoconversion efficiency. Further investigation into the absorbance spectrum of its purified protein reveals that it only has the absorbance peak of the anionic form. Indeed, the His163 is considered to form an electrostatic interaction with the chromophore in mTFP1 (Ai et al., 2006). In contrast, mutant that have higher photoconversion efficiency correspond to higher ratio of neutral form versus anionic form. The absorption spectra of red mClavGR variants are more complicated since it composes that of the red form and that of the unphotoconverted green form. The three peaks at 565 nm, 525 nm and 355 nm are associated with the anionic red form while the 2 peaks at 488 nm and 460 nm are the result of the residue green anionic form as these two peaks are not shown in the excitation spectra. Unlike Dendra2, the neutral form of the red form is not fluorescent. The mClavGR2's oligomeric state is illustrated by the gel filtration chromatography (FIG. 9).

Figure 10:
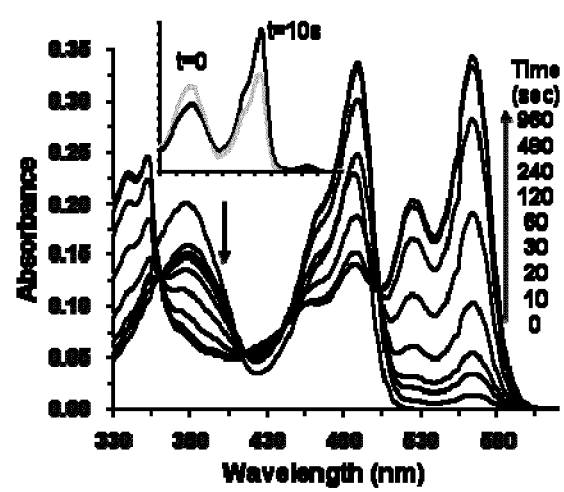
FIG. 10. Absorbance spectra vs. photoconversion time of mClavGR2 in PBS (pH 7.4). Arrows indicate the decrease in neutral green form and increase in anionic red form. Inset shows the absorbance spectra at time 0 (grey) and 10 s (black). There is a substantial shift between the equilibrium.

One interesting property of our mClavGR is that the 408 nm illumination used to photoconvert green form into red form can also shift the neutral green form into anionic green form (FIG. 10). As a result, green fluorescence initially increases upon photoconvertion. The later phenomenon was also observed in Kaede (Chudakov et al., 2007) and Dendra2 (Kremers et al., 2009), but the shifting between neutral green and anionic green form have not been reported.

Of the previously reported green-to-red photoconvertible FPs, mClavGR2 has the highest amino acid similarity and % identity with mEos2 (FIG. 2 and Tables 4 and 5). However, if one considers only those residues with side chains directed toward the interior of the beta-barrel, mClavGR2 is most similar to mKikGR with just 7 conservative amino acid differences (versus 8 for Kaede, 9 for mEos2, and 13 for Dendra2) (Tables 6 and 7). Of the green-to-red fluorescent proteins reported to date, the two that are most similar with respect to the identity of residues directed towards the interior of the beta-barrel are mEos2 and Kaede with just 4 differences. The two that are most divergent are Dendra2 and mKikGR with 17 differences.

TABLE 4

Amino acid similarities (lower triangle) and identities (upper triangle) as calculated using MatGat (40) using the complete protein sequences provided in FIG. 2.

| | mTFP1 | mClavGR1 | mClavGR1.1 | mClavGR2 | mEos2 | Dendra2 | Kaede | mKikGR |
|---|---|---|---|---|---|---|---|---|
| mTFP1 | | 81.9 | 80.2 | 79.3 | 62.4 | 66.9 | 59.1 | 59.3 |
| mClavGR1 | 90.7 | | 97 | 96.6 | 77.6 | 70.2 | 75.1 | 71.5 |
| mClavGR1.1 | 89.9 | 98.7 | | 94.5 | 75.5 | 68.5 | 73.8 | 70.2 |
| mClavGR2 | 89 | 98.3 | 97.9 | | 76.4 | 69.3 | 73.8 | 71.1 |
| mEos2 | 76.3 | 84.4 | 83.5 | 84.4 | | 70.9 | 83.2 | 71.7 |
| Dendra2 | 78 | 81 | 81 | 80.6 | 84.1 | | 67.7 | 64.4 |
| Kaede | 76.3 | 84 | 84 | 83.5 | 91.6 | 82.7 | | 66.1 |
| mKikGR | 77.5 | 84.8 | 83.5 | 84.4 | 83.6 | 80.2 | 80.6 | |

TABLE 5

Amino acid similarities (lower triangle) and identities (upper triangle) as calculated using MatGat (40) using only the sequence from position 6c to 224 in FIG. 2.

| | mTFP1 | mClavGR1.0 | mClavGR1.1 | mClavGR2.0 | mEos2 | Dendra2 | Kaede | mKikGR |
|---|---|---|---|---|---|---|---|---|
| mTFP1 | | 80.5 | 79.2 | 78.3 | 66.5 | 71.8 | 62.4 | 63.2 |
| mClavGR1.0 | 90 | | 97.3 | 96.8 | 82.8 | 74.2 | 79.6 | 76.3 |
| mClavGR1.1 | 89.6 | 99.1 | | 94.1 | 80.5 | 72.4 | 78.3 | 75 |
| mClavGR2.0 | 88.7 | 98.6 | 97.7 | | 81.4 | 73.3 | 78.3 | 75.9 |
| mEos2 | 80.5 | 89.6 | 88.7 | 89.6 | | 71 | 84.2 | 74.1 |
| Dendra2 | 83.2 | 85.1 | 85.1 | 84.6 | 83.7 | | 67.9 | 65.9 |

TABLE 5-continued

Amino acid similarities (lower triangle) and identities (upper triangle) as calculated using MatGat (40) using only the sequence from position 6c to 224 in FIG. 2.

|  | mTFP1 | mClavGR1.0 | mClavGR1.1 | mClavGR2.0 | mEos2 | Dendra2 | Kaede | mKikGR |
|---|---|---|---|---|---|---|---|---|
| Kaede | 79.6 | 88.7 | 88.7 | 88.2 | 92.3 | 82.4 |  | 68.3 |
| mKikGR | 80.7 | 88.8 | 87.4 | 88.3 | 86.1 | 82.1 | 83.4 |  |

TABLE 6

Amino acid differences between green-to-red proteins, considering only those residues with side chains directed towards the interior of the β-barrel. Amino acids that differ from mClavGR2 are shaded gray.

| Position | mClavGR2 | mEos2 | Dendra2 | Kaede | mKikGR |
|---|---|---|---|---|---|
| 14 | I | I | V | I | I |
| 16 | L | L | V | L | L |
| 44 | I | M | A | M | V |
| 52 | A | G | A | A | G |
| 57 | A | A | S | A | A |
| 58 | Y | F | Y | Y | F |
| 65 | F | F | V | F | F |
| 73 | T | A | T | A | V |
| 91 | Y | Y | Y | F | Y |
| 97 | M | L | M | L | M |
| 99 | Y | F | F | F | Y |
| 107 | A | A | I | A | A |
| 109 | N | N | S | N | N |
| 120 | N | N | Q | N | N |
| 122 | I | V | V | V | I |
| 150 | M | M | I | M | M |
| 161 | V | I | I | I | V |
| 183 | V | A | A | S | A |
| 199 | I | I | I | I | M |
| 213 | L | L | L | L | A |
| # differences from mClavGR2 | 0 | 9 | 13 | 8 | 7 |

TABLE 7

Sum of the number of differences between green-to-red proteins, considering only those residues with side chains directed towards the interior of the β-barrel.

|  | mEos2 | Dendra2 | Kaede | mKikGR |
|---|---|---|---|---|
| mClavGR2.0 | 9 | 13 | 8 | 7 |
| mEos2 |  | 13 | 4 | 8 |
| Dendra2 |  |  | 13 | 17 |
| Kaede |  |  |  | 12 |
| mKikGR |  |  |  |  |

One of the most distinctive amino acid differences in close proximity to the chomophore is the residue at position 73. In mClavGR2 and Dendra2 this residue is a Thr, whereas in mEos2 and Kaede it is Ala and in mKikGR it is Val (FIG. 2 and Table 6). It has previously been suggested that hydrogen bonding between the side chain of a Thr at this position and the guanidinium group of the Arg70 sidechain may hold the guanidinium further from the chromophore and thus limit charge stabilization. This diminished degree of charge stabilization in Dendra2 has been used to explain both the blue shifted emission and the higher pKa of the chromophore (Adam et al., 2009). We made several attempts to improve the properties of our mClavGR variants by introducing substitutions at position 73. When we generated a library of all possible substitutions at position 73 and screened it in colony to identify the variants that exhibited the highest green fluorescence before photoconversion and the highest red fluorescence after photoconversion, we found that the 'best' colonies retained Thr at position 73. We also created the Thr73Ala and Thr73Val variants individually and characterized them. When expressed in *E. coli*, the green form of the Thr73Ala variant was approximately equivalent in brightness to the Thr73 progenitor, but the red (photoconverted) form was substantially dimmer. For the Thr73Val variant, both the green and red forms were substantially dimmer than the original Thr73 variant.

Figure 6:
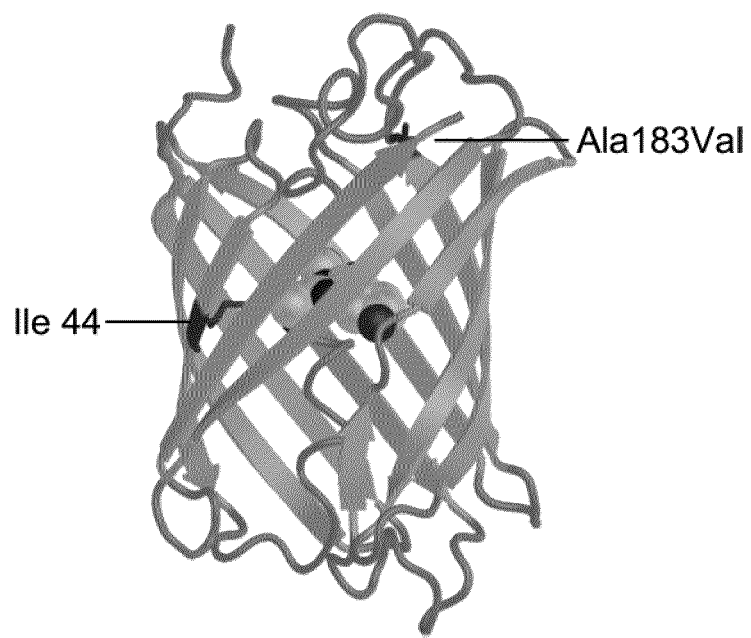
FIG. 6. Location of substitutions in mClavGR2 that are unique among green-to-red photoconvertible FPs. The molecular structure of mTFP1 (PDB ID 2HQK) is represented here (Ai et al., 2006).

There are just two residues of mClavGR2 that are directed towards the interior of the beta-barrel and that have amino acid identities that are not found in anyone of the other green-to-red photoconvertible FPs (FIG. 6). These residues are Ile44 (Met, Ala, and Val in other photoconvertible FPs) and the Val 183 (Ala and Ser in others). The valine at position 183 is the result of an amino acid substitution (Ala183Val) identified through screening of randomly mutated libraries for improved brightness and photoconversion. This is located near one end of the 9th beta-strand of the protein and is relatively distant from the chromophore. Given its distant location, it is unlikely to be having a direct influence on the properties of the chromophore and is more likely contributing to improved brightness by increasing the folding efficiency of the protein. In contrast, Ile44 is in very close proximity to the chromophore and is likely interacting with the side chain of His66 (FIG. 1), which is an integral part of the red chromophore. We generated saturation library at Ile44 and again found the best-performing variant remains Ile. We then tried an Ile44Met/Val library and found out the substituent of Met lead to poor photoconversion efficiency, while 44Val has subtlety weaker fluorescence in both form.

Evolution of KikGR for brighter red fluorescence following illumination with 365 nm light, produced a protein with its phenol/phenolate equilibrium dramatically shifted towards the neutral form at pH 7.4 (Tsutsui et al., 2005). This shift in equilibrium is described by an increase in the apparent pKa of the chromophore from 4.2 for the wild-type progenitor to 7.8 for KikGR. The authors speculate that a high pKa is essential for efficient photoconversion, since a greater fraction of the protein exists in the protonated state from which the photoconversion reaction is initiated. Likewise, the higher pKa of Dendra2 relative to EosFP means that a much greater fraction of the protein exists in the protonated ground state at neutral pH and thus the photoconversion efficiency is improved (Adam et al., 2009).

Figure 8A:
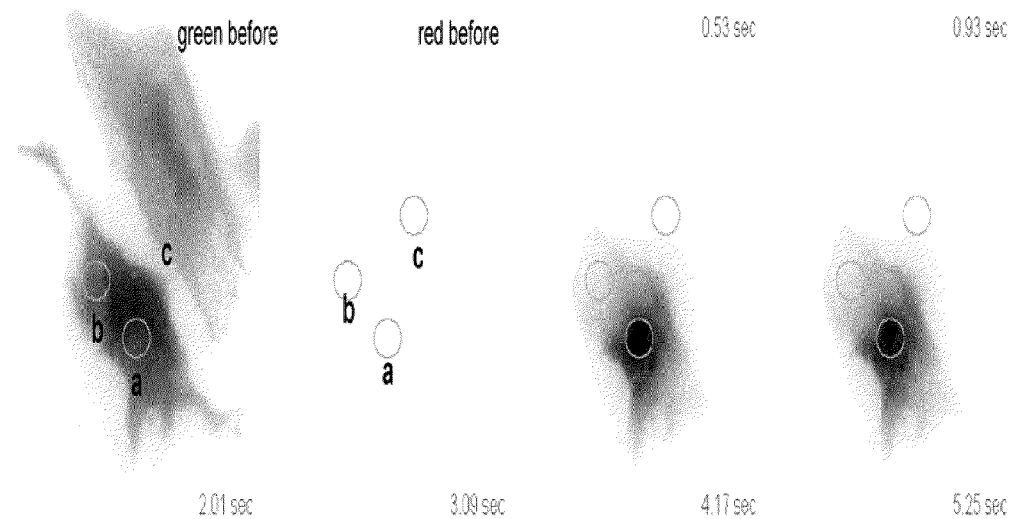
FIGS. 8A thru 8C. Imaging protein diffusion with mClavGR2. (A) Images of two cells expressing mClavGR2, prior to photoconversion. (B) A series of images showing the free diffusion of photoconverted mClavGR2 following exposure to a 408 nm laser for 2 seconds (the laser beam was centered close to position a). (C) Red fluorescent intensity vs. time in each of the 3 areas of interest indicated in panel (A). Solid black line is the mean intensity of area a; the solid grey line is the mean intensity of area b; and the dashed black line is the mean intensity of area c.
Figure 8C:
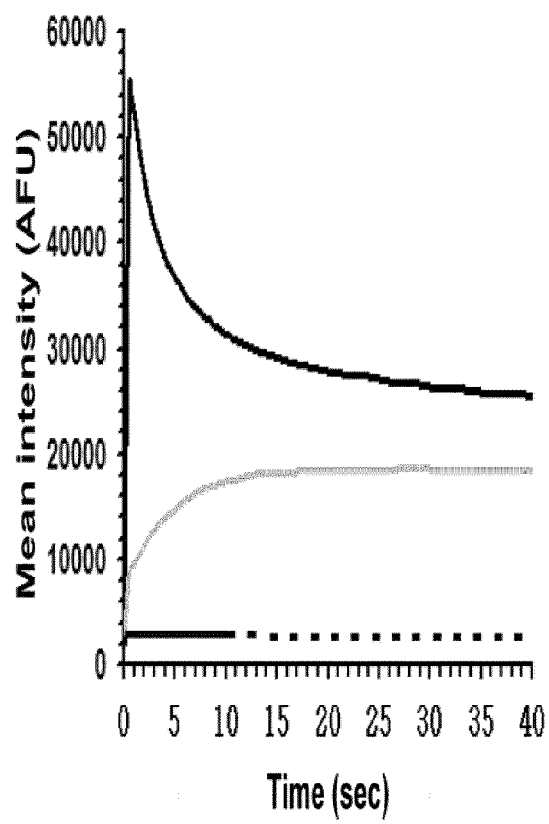
Figure 8B:
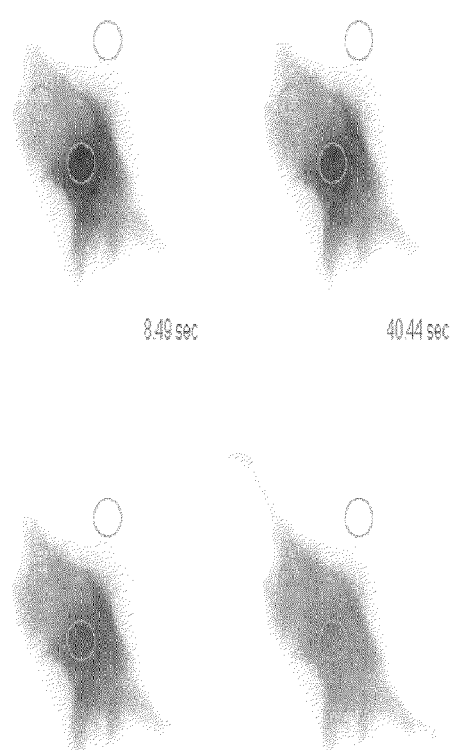

The monomeric state of mClavGR2 is again illustrated by the fine filament structure of mClavGR2-β-actin fusion expressed in Hela cells (FIG. 7A). In order to test the application of mClavGR2 as a "cell tracker", we expressed mClavGR2 in Hela cells either with targeting to the nucleus or with no targeting. Photoconversion of mClavGR2 targeted to the nucleus was used to highlight specific cells within a population (FIG. 7B). mClavGR2 expressed with no targeting sequence, accumulates in the cytoplasm as expected. We then photoconverted a limited area using a 408 nm laser for 2 seconds and subsequently acquired images in the red channel. It can be clearly seen the red fluorescence corresponding to the photoconverted mClavGR2 which was originally in area A (FIG. 8) diffused into the whole cell, indicating mClavGR2 could be readily used to study fast dynamics of proteins inside living cell.

We have developed and characterized a new green-to-red photoconvertible FP variant known as mClavGR2. Our results demonstrate that mClavGR2 has a monomeric structure, in the constructs tested to date, does not interfere with the correct localization of a genetically fused protein partner.

As used herein, a "nucleic acid" or "polynucleotide" includes a nucleic acid, an oligonucleotide, a nucleotide, a polynucleotide, and any fragment, variant, or derivative thereof. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthine hypoxanthine. The nucleic acid or polynucleotide may be combined with a carbohydrate, a lipid, a protein, or other materials. A nucleic acid sequence of interest may be chemically synthesized using one of a variety of techniques known to those skilled in the art, including, without limitation, automated synthesis of oligonucleotides having sequences which correspond to a partial sequence of the nucleotide sequence of interest, or a variation sequence thereof, using commercially-available oligonucleotide synthesizers, such as the Applied Biosystems Model 392 DNA/RNA synthesizer.

One nucleic acid composition of the present invention is the nucleotide sequence encoding mClavGR2 (SEQ ID NO: 1). Accordingly, in one embodiment of the present invention, the isolated nucleic acid composition comprises a nucleic acid sequence having at least about 90% homology with the nucleotide sequence of SEQ ID NO: 1. In another embodiment of the present invention, the isolated nucleic acid encodes a polypeptide sequence having at least about 95% homology with the polypeptide encoded by the nucleotide sequence of SEQ ID NO: 1. In still another embodiment of the present invention, the isolated nucleic acid composition comprises a nucleic acid sequence that is substantially the same as, or identical to, the nucleotide sequence of SEQ ID NO: 1. In one embodiment, the nucleic acid composition comprises any nucleic acid sequence which encodes any protein of the present invention, including proteins having the amino acid sequence SEQ ID NO: 2 and its variations and mutations described herein. In certain embodiments, the nucleic acid sequence may be re-synthesized such that it is compatible with mammalian (e.g., human) codon usage, or the sequence may be resynthesized to be optimized for non-mammalian codon preferences.

The present invention further provides an isolated nucleic acid, including any mimetic or complement thereof, that hybridizes under stringent conditions to the nucleic acid composition described herein. The "complement" of a nucleic acid sequence refers, herein, to a nucleic acid molecule which is completely complementary to another nucleic acid, or which will hybridize to the other nucleic acid under conditions of stringency. Stringent (e.g., high-stringency) conditions are known in the art. Stringent conditions are sequence-dependent, and may vary depending upon the circumstances.

The present invention further provides a method of engineering a nucleic acid sequence encoding a non-oligomerizing photoconvertible fluorescent protein having a tyrosine-derived chromophore, by screening a fully-synthetic gene library. In one embodiment, the gene library comprises the nucleotide sequence of SEQ ID NO: 1.

The present invention also provides a vector comprising a nucleic acid sequence encoding the non-oligomerizing photoconvertible fluorescent protein having a tyrosine-derived chromophore described herein. Also provided is a host cell (e.g., a mammalian cell) comprising the vector.

In one embodiment of the present invention, the vector is a plasmid, although it is to be understood that other types of vectors, such as cosmids and phagemids, may also be used for the purposes of the present invention. The term "plasmid", as used herein, refers generally to circular double-stranded DNA, which is not bound to a chromosome. The DNA may be a chromosomal or episomal-derived plasmid. The plasmid of the present invention may optionally contain a terminator of transcription; a promoter; and/or a discrete series of restriction-endonuclease recognition sites, located between the promoter and the terminator. In the plasmid, a polynucleotide insert of interest (e.g., one encoding mClavGR2) should be operatively linked to an appropriate promoter, such as its native promoter or a host-derived promoter, such as the *E. coli* lacZ promoters, the trp and tac promoters, the T3 and T7 promoters, or the CMV promoters. Other suitable promoters will be known to the skilled artisan.

The vector of the present invention may comprise cDNA encoding mClavGR2. As used herein, the term "cDNA" refers to an isolated DNA polynucleotide or nucleic acid molecule, or any fragment, derivative, or complement thereof. The cDNA may be double-stranded, single-stranded, or triple-stranded, it may have originated recombinantly or synthetically, and it may represent coding and/or noncoding 5' and/or 3' sequences.

The vector of the present invention may be useful in a method for expressing the nucleic acid sequence in mammalian cells or non-mammalian cells. In one embodiment, the nucleic acid of the vector is expressed as a tandem genetic fusion to another protein.

The present invention further provides a non-oligomerizing photoconvertible fluorescent protein comprising a tyrosine-derived chromophore, as well as any derivative, fragment, or homologue thereof.

Furthermore, the photoconvertible fluorescent protein of the present invention may comprise an amino acid sequence having at least about 95% homology with the amino acid sequence of SEQ ID NO: 2 (FIG. 2). In another embodiment, the FP variant comprises an amino acid sequence, which is substantially the same as, or identical to, the amino acid sequence of SEQ ID NO: 2 (FIG. 2).

Additionally, the present invention provides an antibody that specifically binds to mClavGR2 and its derivatives, as described herein. The antibody of the present invention may be polyclonal or monoclonal, and may be produced by techniques well known to those skilled in the art. Polyclonal antibody, for example, may be produced by immunizing a mouse, rabbit, or rat with purified protein. Monoclonal antibody then may be produced by removing the spleen from the immunized mouse, rabbit, or rat, and fusing the spleen cells with myeloma cells to form a hybridoma which, when grown in culture, will produce a monoclonal antibody.

The antibodies used herein may be labeled with a detectable marker or label. Labeling of an antibody may be accomplished using one of a variety of labeling techniques, including peroxidase, chemiluminescent labels known in the art, and radioactive labels known in the art. The detectable marker or label of the present invention may be, for example, a non-radioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker or label may be a radioactive marker, including, for example, a radioisotope. The radioisotope may be any isotope that emits detectable radiation. Radioactivity emitted by the radioisotope can be detected by techniques well known in the art. For example, gamma emission from the radioisotope may be detected using gamma imaging techniques, particularly scintigraphic imaging.

The present invention is described in the following Examples, which are set forth to aid in the understanding of the invention, and should not be construed to limit in any way the scope of the invention as defined in the claims which follow thereafter.

EXAMPLES

Example 1

General Methods and Materials

All synthetic DNA oligonucleotides for cloning and library construction were purchased from Integrated DNA Technologies (Coralville, Iowa). PCR products and products of restriction digests were purified using QIA gel extraction kit (Qiagen) according to the manufacturer's protocols. Restriction enzymes were purchased from New England. Biolabs. The cDNA sequences for all mClavGR variants were confirmed by dye terminator cycle sequencing using the DYEnamic ET kit (Amersharn Biosciences) or BigDye Terminator v3.1 Cycle Sequencing Kit (Applied Biosystems). Sequencing reactions were analyzed at the University of Alberta Molecular Biology Service Unit.

Example 2

Plasmid Library Creation and Site-Directed Mutagenesis

In order to produce the designed cDNA encoding mClavGR1, 14 forward and 14 reverse oligonucleotides with 51 bases each were synthesized and assembled using circular assembly amplification (31). A forward primer with XhoI and a reverse primer with EcoRI restriction site were used to amplify the cDNA, which was subsequently digested and ligated into similarly digested pBAD/His B vector (Invitrogen). Randomly mutated libraries were created by error prone PCR, where dNTPs mix with a deficient component were used and MnCl2 were added to the reaction to further decrease the fidelity of Taq polymerase (30). Saturation/semi-saturation mutagenesis at specific residues were created through overlapping PCR as previously described (30). Conditions for staggered extension process (StEP) PCR were optimized for the length of mClavGR (714 bp) to give a recombination efficiency of 1 mutation per 100 bp (32). Specifically, a total of 0.1 pmol pBAD/His B plasmids containing DNA sequence of 5-15 mClavGR variants selected from randomly mutated libraries were used as the template mix. The mixture was subjected to 100 thermal cycles (94° C. for 45 s then 55° C. for 5 s), followed by an extra extension step at 72° C. for 5 min. Regardless of library assembly method (i.e., error prone PCR, saturation mutagenesis, or StEP PCR), gene libraries were inserted into pBAD/His B between the Xho I and EcoRI sites as described above. Electrocompetent *Escherichia coli* strain DH10B (Invitrogen) was transformed and plated on LB (Luria-Bertani)/agar plates supplemented with ampicillin (0.1 mg/ml) and L-arabinose (0.02%). Plates were incubated for 14 h at 37° C. prior to screening.

Example 3

Library Screening

*E. coli* colonies expressing the mClavGR libraries were grown on 10 cm Petri dishes. Photoconversion was conducted using a custom-built "photoconversion chamber" which is described in Results. Filter sets of 470/40 nm, 510/20 nm and 560/40 nm, 630/60 nm (Chroma) were used to acquire the green and red fluorescence images, respectively, before and after photoconversion.

Example 4

Protein Purification and Characterization

Protein purification was carried as previously described (Ai et al., 2006) and the buffer was changed into phosphate buffered saline (PBS, pH 7.4). Molar extinction coefficients ($\Sigma$) of the green forms were measured by the alkali denaturation method (Shaner et al., 2004; Ward, 1998) and then used as reference to measure $\Sigma$ for the red forms. Fluorescence quantum yields ($\sqrt{}$) were determined using fluorescein in 10 nM NaOH ($\sqrt{}=0.95$) (Brannon, 1978) and Rhodamine 6G in ethanol ($\sqrt{}=0.94$) (Fischer, 1996) as standards.

To determine the relative quantum yields for photoconversion, each purified variant's absorbance at 487 nm was measured to determine their concentration. The proteins were then converted into the red form by the same illumination system used for screening for 1 minute. The photoconverted proteins' absorbance at 565 nm was measured to determine the concentration of the photoconverted red species. The proteins were then diluted 10-fold into PBS and their red fluorescence was recorded. The photoconversion quantum yield relative to mClavGR1 ($\sqrt{}_{PC,GRX}/\sqrt{}_{PC,GR1}$) was calculated using Equation 1.

$$\frac{\Phi_{PC,GRX}}{\Phi_{PC,GR1}} = \frac{c_{red,GRX}/c_{green,GRX}}{c_{red,GR1}/c_{green,GR1}} = \frac{A_{565,GRX}/\varepsilon_{565,GRX}}{A_{487,GRX}/\varepsilon_{487,GRX}} * \frac{A_{487,GR1}/\varepsilon_{487,GR1}}{A_{565,GR1}/\varepsilon_{565,GR1}}$$

Equation 1

In Equation 1, A487, A565, $\Sigma$487, and $\Sigma$565, are the absorbance and extinction coefficients at 487 nm (before photoconversion) and 565 nm (after photoconversion), respectively. 'GR1' refers to mClavGR1, while GRX refers to one of the other variants. This relative photoconversion quantum yield gives the frequency of generating of the red species of the evolved variants relative to the parent mClavGR1 when illuminated by the screening system. A relative photoconversion effectiveness ($E_{PC,GRX}/E_{PC,GR1}$) was calculated using Equation 2, again with mClavGR1 as reference.

$$\frac{E_{PC,GRX}}{E_{PC,GR1}} = \frac{c_{GR1}}{c_{GRX}} * \frac{I_{GRX}}{I_{GR1}} \qquad \text{Equation 2}$$

In Equation 2, c is the concentration of the purified protein solution and I is the red fluorescence intensity following photoconversion. This relative photoconversion efficiency measure the efficiency of the photoconversion when illuminated by the screening system, counting factors such as ratio of neutral form versus ionic form at the beginning and brightness of the red form. All absorption measurement was acquired on a DU-800 UV-visible spectrophotometer (Beckman). All fluorescence spectra were recorded on a QuantaMaster spectrofluorimeter (Photon Technology International) and have been corrected for the detector response.

For determination of the pH dependence, purified protein in PBS was diluted 1:50 into citrate saline buffer (pH<8 or =8) or sodium phosphate buffer (pH>8) in a 96-well black clear bottom plate (Corning). Fluorescence was measured using a Safire2 plate reader (Tecan). The oligomeric structure of mClavGR variants was determined by gel filtration chromatography with a HiLoad 16/60 Superdex 75 pg gel filtration column on an AKTAbasic liquid chromatography system (GE Healthcare). Samples of the dimeric dTomato and the monomeric mCherry proteins (34) were expressed and purified in the same way as mClavGR variants and used as size standards. Purified mClavGR variants were mixed with dTomato (or mCherry) and the resulting elution profiles were monitored at both 488 nm and 555 nm (or 585 nm for mCherry).

Example 5

Mammalian Expression Vectors

To create the mClavGR2-actin and mClavGR2-NLS vectors, the gene encoding mClavGR2 was amplified with a 5' primer with a NheI site and a 3' primer with a XhoI site. The purified PCR products were then digested and ligated into pEGFP-actin and pEYFP-NLS (Clontech), whose FP-coding gene has been previously removed by same restriction enzymes. To create the mClavGR2 vector for cytoplasmic expression, the mClavGR2 gene was inserted between the XhoI and EcoRI restriction sites of a pcDNA3 vector (Invitrogen) in which the multiple cloning site had been modified to contain XhoI and EcoRI restriction sites in the same reading frame as the same sites in pBAD/His B.

Example 6

Cell Culture and Transfection

Hela cells were maintained in Dulbecco's Modified Eagle Medium (DMEM) (Invitrogen) supplemented with 10% heat-inactivated fetal calf serum (Invitrogen) and 2 mM GlutaMax (Invitrogen) at 37° C. and 5% CO2. Plasmid DNA for transfection was prepared by Qiagen Plasmid Midi Kit (Qiagen) according to the manufacturer's protocol. Lipofectamine 2000 (Invitrogen) was used as transfection reagent. Cells for transfection and imaging were cultured on a 35 mm glass-bottom culture dish. We follow the tranfection protocol recommended by the manufacturer except the following conditions: 3 µg of plasmid DNA and 7.5 µl of Lipofectamine 2000 were used; incubation time of the cell with transfection reagent was shortened to 2.5 h. The medium was changed into HEPEs-buffered Hank's Buffered Salt Solution (HHBSS) (Invitrogen) before imaging. Imaging was done 24-36 h after the start of transfection.

Example 7

Live Cell Imaging

Microscopy was performed using an inverted Nikon Eclipse Ti microscope equipped with an QuantEM 512SC electron-multiplying CCD (Photometrics), a 75W Xeon lamp for epi-fluorescence illumination, and a 408 nm photoactivation laser with a power of >500 mW (Melles Griot). A 63× oil-immersed objective (Nikon) was used for all imaging. Green fluorescence was measured using a 450-490 nm bandpass excitation filter, a 495 nm longpass beam splitter, and a 500-550 nm bandpass emission filter. Red fluorescence was measured using a 528-553 nm bandpass excitation filter, a 565 nm longpass beam splitter, and a 590-650 nm bandpass emission filter (Chroma).

While the foregoing invention has been described in some detail for purposes of clarity and understanding, it will be appreciated by one skilled in the art, from a reading of the disclosure, that various changes in form and detail can be made without departing from the true scope of the invention in the appended claims.

References

The following references are referred to by first author's last name and year of publication, in parenthesis, in the above description and are incorporated herein as if reproduced in their entirety.

Adam, V., Nienhaus, K., Bourgeois, D., and Nienhaus, G. U. (2009). Structural basis of enhanced photoconversion yield in green fluorescent protein-like protein Dendra2. Biochemistry 48, 4905-4915.

Ai, H. W., Henderson, J. N., Remington, S. J., and Campbell, R. E. (2006). Directed evolution of a monomeric, bright and photostable version of Clavularia cyan fluorescent protein: structural characterization and applications in fluorescence imaging. The Biochemical journal 400, 531-540.

Ando, R., Hama, H., Yamamoto-Nino, M., Mizuno, H., and Miyawaki, A, (2002). An optical marker based on the UV-induced green-to-red photoconversion of a fluorescent protein. Proc Natl Acad Sci USA 99, 12651-12656.

Brannon, J. H., and Magde, D. (1978). Absolute Quantum Yield Determination by Thermal Blooming—Fluorescein. J Phys Chem 82, 705-709.

Campbell, R. E., Tour, O., Palmer, A. E., Steinbach, P. A., Baird, G. S., Zacharias, D. A., and Tsien, R. Y. (2002). A monomeric red fluorescent protein. Proc Natl Acad Sci USA 99, 7877-7882.

Chattoraj, M., King, B. A., Bublitz, G. U., and Boxer, S. G. (1996). Ultra-fast excited state dynamics in green fluorescent protein: multiple states and proton transfer. Proc Natl Acad Sci USA 93, 8362-8367.

Chudakov, D. M., Lukyanov, S., and Lukyanov, K. A. (2007). Tracking intracellular protein movements using photoswitchable fluorescent proteins PS-CFP2 and Dendra2. Nature protocols 2, 2024-2032.

Fischer, M., and Georges, J. (1996). Fluorescence quantum yield of Rhodamine 6G in ethanol as a function of concentration using thermal lens spectrometry. Fluorescence quantum yield of Rhodamine 6G in ethanol as a function of concentration using thermal lens spectrometry 260, 115-118.

Gurskaya, N. G., Verkhusha, V. V., Shcheglov, A. S., Staroverov, D. B., Chepurnykh, T. V., Fradkov, A. F., Lukyanov, S., and Lukyanov, K. A. (2006). Engineering of a monomeric green-to-red photoactivatable fluorescent protein induced by blue light. Nature biotechnology 24, 461-465.

Habuchi, S., Tsutsui, H., Kochaniak, A. B., Miyawaki, A., and van Oijen, A. M. (2008). mKikGR, a monomeric photoswitchable fluorescent protein. PloS one 3, e3944.

Kremers, G. J., Hazelwood, K. L., Murphy, C. S., Davidson, M. W., and Piston, D. W. (2009). Photoconversion in orange and red fluorescent proteins. Nature methods 6, 355-358.

McKinney, S. A., Murphy, C. S., Hazelwood, K. L., Davidson, M. W., and Looger, L. L. (2009). A bright and photostable photoconvertible fluorescent protein. Nature methods 6, 131-133.

Mizuno, H., Mal, T. K., Tong, K. I., Ando, R., Furuta, T., Ikura, M., and Miyawaki, A. (2003). Photo-induced peptide cleavage in the green-to-red conversion of a fluorescent protein. Molecular cell 12, 1051-1058.

Nienhaus, G. U., Nienhaus, K., Holzle, A., Ivanchenko, S., Renzi, F., Oswald, F., Wolff, M., Schmitt, F., Rocker, C., Vallone, B., et al. (2006). Photoconvertible fluorescent protein EosFP: biophysical properties and cell biology applications. Photochemistry and photobiology 82, 351-358.

Ormo, M., Cubiti, A. B., Kallio, K., Gross, L. A., Tsien, R. Y., and Remington, S. J. (1996). Crystal structure of the Aequorea victoria green fluorescent protein. Science (New York, N.Y. 273, 1392-1395.

Shaver, N. C., Campbell, R. E., Steinbach, P. A., Giepmans, B. N., Palmer, A. E., and Tsien, R. Y. (2004). Improved monomeric red, orange and yellow fluorescent proteins derived from *Discosoma* sp. red fluorescent protein. Nature biotechnology 22, 1567-1572.

Tsutsui, H., Karasawa, S., Shimizu, H., Nukina, N., and Miyawaki, A. (2005). Semi-rational engineering of a coral fluorescent protein into an efficient highlighter. EMBO reports 6, 233-238.

Tsutsui, H., Shimizu, H., Mizuno, H., Nukina, N., Furuta, T., and Miyawaki, A. (2009). The E1 mechanism in photo-induced beta-elimination reactions for green-to-red conversion of fluorescent proteins. Chemistry & biology 16, 1140-1147.

Ward, W. W. (1998). Biochemical and physical properties of GFP, in Green Fluorescent Protein Properties, Applications, and Protocols (New York, Wiley).

Wiedemann, J., Ivanchenko, S., Oswald, F., Schmitt, F., Rocker, C., Salih, A., Spindler, K. D., and Nienhaus, G. U. (2004). EosFP, a fluorescent marker protein with UV-inducible green-to-red fluorescence conversion. Proc Natl Acad Sci USA 101, 15905-15910.

What is claimed is:

1. An isolated nucleic acid encoding the amino acid sequence of SEQ ID NO: 2.

2. The isolated nucleic acid of claim 1, wherein the nucleic acid comprises the nucleotide sequence of SEQ ID NO:1.

3. An isolated nucleic acid molecule encoding a photoconvertible chromoprotein or fluorescent protein, wherein said nucleic acid has a sequence identity of at least 90% with SEQ ID NO:1.

4. An isolated nucleic acid encoding a chromo- or fluorescent protein, wherein said protein has a sequence identity of at least 95% with SEQ ID NO: 2.

5. The isolated nucleic acid of claim 1, wherein the encoded polypeptide is a monomer.

6. The nucleic acid sequence of claim 1 which is compatible with mammalian codon usage.

7. The nucleic acid sequence of claim 1 which is compatible with human codon usage.

8. A vector comprising a nucleic acid of any one of claims 1, 2, 3, 4, 5, 6, and 7.

9. The vector of claim 8, which is a plasmid.

10. The vector of claim 9, wherein the nucleic acid sequence is cDNA.

11. An isolated host cell comprising the vector of claim 8.

12. A kit comprising the polynucleotide sequence of claim 1.

13. A transgenic animal comprising a nucleic acid molecule having a sequence identity of at least 90% with SEQ ID NO:1, whereby said nucleic acid molecule encodes a photoconvertible chromoprotein or fluorescent protein.

14. A transgenic plant comprising a nucleic acid molecule having a sequence identity of at least 90% with SEQ ID NO:1, whereby said nucleic acid molecule encodes a photoconvertible chromoprotein or fluorescent protein.

15. A photoconvertible chromoprotein or fluorescent protein encoded by the nucleic acid of claim 3.

16. A chromo- or fluorescent protein encoded by the nucleic acid of claim 4.

17. A kit comprising the polypeptide encoded by the polynucleotide of claim 1.

18. The photoconvertible chromoprotein or fluorescent protein of claim 15 or 16 wherein the protein is a monomer or a dimer.

19. The photoconvertible chromoprotein or fluorescent protein of claim 18 wherein the protein comprises the amino acid sequence tyrosine-glycine (YG).

20. The protein of claim 19 wherein the protein comprises one or more of the amino acid sequence His-Tyr-Gly, glutamine-tyrosine-glycine (QYG); alanine-tyrosine-glycine (AYG), cysteine-tyrosine-glycine (CYG), glycine-tyrosine-glycine (GYG) or serine-tyrosine-glycine (SYG).

21. The protein of claim 20 wherein the polypeptide comprises at least one or more of the following mutations T6bI, T41I, D77E, F99Y, K115E, E127T, K139R, A183V, H220R, S221N, G222S, L223T, Pub224D.

* * * * *

SEQUENCE LISTING

```
<160> NUMBER OF SEQ ID NOS: 11

<210> SEQ ID NO 1
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide based on modified/derived Clavularia

<400> SEQUENCE: 1
atggtgagca agggcgagga gaccatcatg agcgtgatca agcctgacat gaagatcaag      60
ctgcgcatgg agggcaacgt gaacggccac gccttcgtga tcgagggcga gggcagcggc     120
aagcccttcg agggcatcca gacgattgat ttggaggtga aggagggcgc cccgctgccc     180
ttcgcctacg acatcctgac caccgccttc cactacggca accgcgtgtt caccaagtac     240
cccgaggaca tccctgacta cttcaagcag agcttccccg agggctacag ctgggagcgc     300
agcatgacct acgaggacgg cggcatctgc atcgccacca cgacatcac gatggaggag      360 gacagcttca tcaacaagat ccacttcaag ggcacgaact tcccccccaa cggcccgtg      420 atgcagaaga ggaccgtggg ctgggaggcc agcaccgaga agatgtacgt gcgcgacggc     480
gtgctgaagg gcgacgtgaa gatgaagctg ctgctgaagg gcggcggcca ctaccgctgc     540
gacttccgca ccacctacaa ggtcaagcag aaggccgtaa agctgcccga ctaccacttc     600
gtggaccacc gcatcgagat cctgagccac gacaaggact acaacaaggt gaagctgtac     660
gagcacgccg tggcccacag cggcctgccc ggcatggacg agctgtacaa gtaa          714

<210> SEQ ID NO 2
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide based on modified/derived Clavularia

<400> SEQUENCE: 2
```

```
Met Val Ser Lys Gly Glu Glu Thr Ile Met Ser Val Ile Lys Pro Asp
1               5                   10                  15

Met Lys Ile Lys Leu Arg Met Glu Gly Asn Val Asn Gly His Ala Phe
            20                  25                  30

Val Ile Glu Gly Glu Gly Ser Gly Lys Pro Phe Glu Gly Ile Gln Thr
            35                  40                  45

Ile Asp Leu Glu Val Lys Glu Gly Ala Pro Leu Pro Phe Ala Tyr Asp
50                  55                  60

Ile Leu Thr Thr Ala Phe His Tyr Gly Asn Arg Val Phe Thr Lys Tyr
65                  70                  75                  80

Pro Glu Asp Ile Pro Asp Tyr Phe Lys Gln Ser Phe Pro Glu Gly Tyr
                85                  90                  95

Ser Trp Glu Arg Ser Met Thr Tyr Glu Asp Gly Gly Ile Cys Ile Ala
            100                 105                 110

Thr Asn Asp Ile Thr Met Glu Glu Asp Ser Phe Ile Asn Lys Ile His
            115                 120                 125

Phe Lys Gly Thr Asn Phe Pro Pro Asn Gly Pro Val Met Gln Lys Arg
130                 135                 140

Thr Val Gly Trp Glu Ala Ser Thr Glu Lys Met Tyr Val Arg Asp Gly
145                 150                 155                 160

Val Leu Lys Gly Asp Val Lys Met Lys Leu Leu Leu Lys Gly Gly Gly
                165                 170                 175

His Tyr Arg Cys Asp Phe Arg Thr Thr Tyr Lys Val Lys Gln Lys Ala
            180                 185                 190

Val Lys Leu Pro Asp Tyr His Phe Val Asp His Arg Ile Glu Ile Leu
                195                 200                 205

Ser His Asp Lys Asp Tyr Asn Lys Val Lys Leu Tyr Glu His Ala Val
            210                 215                 220

Ala His Ser Gly Leu Pro Gly Met Asp Glu Leu Tyr Lys
225                 230                 235

<210> SEQ ID NO 3
<211> LENGTH: 236
<212> TYPE: PRT
<213> ORGANISM: Artificial Sequence
<220> FEATURE:
<223> OTHER INFORMATION: Description of Artificial Sequence: Synthetic
      Clavularia cyan fluorescent protein variant mTFP1
      polypeptide

<400> SEQUENCE: 3

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
            35                  40                  45

Ile Asn Leu Glu Val Lys Glu Gly Ala Pro Leu Pro Phe Ser Tyr Asp
50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110
```

```
Lys Ser Asp Ile Ser Met Glu Glu Asp Ser Phe Ile Tyr Glu Ile His
            115                 120                 125

Leu Lys Gly Glu Asn Phe Pro Pro Asn Gly Pro Val Met Gln Lys Lys
        130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Glu Gly Gly Gly
            165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys
225                 230                 235

<210> SEQ ID NO 4
<211> LENGTH: 237
<212> TYPE: PRT
<213> ORGANISM: Artificial Sequence
<220> FEATURE:
<223> OTHER INFORMATION: Description of Artificial Sequence: Synthetic
      Clavularia cyan fluorescent protein variant mCLAVGR1.0
      polypeptide

<400> SEQUENCE: 4

Met Val Ser Lys Gly Glu Glu Thr Thr Met Ser Val Ile Lys Pro Asp
1               5                   10                  15

Met Lys Ile Lys Leu Arg Met Glu Gly Asn Val Asn Gly His Ala Phe
            20                  25                  30

Val Ile Glu Gly Glu Gly Ser Gly Lys Pro Phe Glu Gly Thr Gln Thr
        35                  40                  45

Ile Asp Leu Glu Val Lys Glu Gly Ala Pro Leu Pro Phe Ala Tyr Asp
    50                  55                  60

Ile Leu Thr Thr Ala Phe His Tyr Gly Asn Arg Val Phe Thr Lys Tyr
65                  70                  75                  80

Pro Asp Asp Ile Pro Asp Tyr Phe Lys Gln Ser Phe Pro Glu Gly Tyr
                85                  90                  95

Ser Trp Glu Arg Ser Met Thr Phe Glu Asp Gly Gly Ile Cys Ile Ala
            100                 105                 110

Thr Asn Asp Ile Thr Met Glu Lys Asp Ser Phe Ile Asn Lys Ile His
            115                 120                 125

Phe Lys Gly Glu Asn Phe Pro Pro Asn Gly Pro Val Met Gln Lys Lys
        130                 135                 140

Thr Val Gly Trp Glu Ala Ser Thr Glu Lys Met Tyr Val Arg Asp Gly
145                 150                 155                 160

Val Leu Lys Gly Asp Val Lys Met Lys Leu Leu Leu Lys Gly Gly Gly
            165                 170                 175

His Tyr Arg Cys Asp Phe Arg Thr Thr Tyr Lys Ala Lys Gln Lys Ala
            180                 185                 190

Val Lys Leu Pro Asp Tyr His Phe Val Asp His Arg Ile Glu Ile Leu
        195                 200                 205

Ser His Asp Lys Asp Tyr Asn Lys Val Lys Leu Tyr Glu His Ala Val
    210                 215                 220

Ala His Ser Gly Leu Pro Gly Met Asp Glu Leu Tyr Lys
                    230                 235
```

```
                                  225                 230                 235

<210> SEQ ID NO 5
<211> LENGTH: 237
<212> TYPE: PRT
<213> ORGANISM: Artificial Sequence
<220> FEATURE:
<223> OTHER INFORMATION: Description of Artificial Sequence: Synthetic
      Monomeric photoconvertible fluorescent protein variant
      mCLAVGR1.1 polypeptide

<400> SEQUENCE: 5

Met Val Ser Lys Gly Glu Glu Thr Ile Met Ser Val Ile Lys Pro Asp
1               5                   10                  15

Met Lys Ile Lys Leu Arg Met Glu Gly Asn Val Asn Gly His Ala Phe
            20                  25                  30

Val Ile Glu Gly Glu Gly Arg Gly Arg Pro Phe Glu Gly Thr Gln Thr
        35                  40                  45

Ile Asp Leu Glu Val Lys Glu Gly Ala Pro Leu Pro Phe Ala Tyr Asp
50                  55                  60

Ile Leu Thr Thr Ala Phe His Tyr Gly Asn Arg Val Phe Thr Arg Tyr
65                  70                  75                  80

Pro Asp Asp Ile Pro Asp Tyr Phe Lys Gln Ser Phe Pro Glu Gly Tyr
                85                  90                  95

Ser Trp Glu Arg Ser Met Thr Phe Glu Asp Gly Gly Ile Cys Ile Ala
            100                 105                 110

Thr Asn Asp Ile Thr Ile Glu Lys Asp Ser Phe Ile Asn Lys Ile His
        115                 120                 125

Phe Lys Gly Glu Asn Phe Pro Pro Asn Gly Pro Val Met Gln Lys Lys
130                 135                 140

Thr Val Gly Trp Glu Ala Ser Thr Glu Lys Met Tyr Val Arg Asp Gly
145                 150                 155                 160

Val Leu Lys Gly Asp Val Lys Met Lys Leu Gln Leu Lys Gly Gly Gly
                165                 170                 175

His His Arg Cys Asp Phe Arg Thr Thr Tyr Lys Ala Lys Gln Lys Ala
            180                 185                 190

Val Lys Leu Pro Asp Tyr His Phe Val Asp His Arg Ile Glu Ile Leu
        195                 200                 205

Ser His Asp Lys Asp Tyr Asn Lys Val Lys Leu Tyr Glu His Ala Val
210                 215                 220

Ala His Ser Gly Leu Pro Gly Met Asp Glu Leu Tyr Lys
225                 230                 235

<210> SEQ ID NO 6
<211> LENGTH: 226
<212> TYPE: PRT
<213> ORGANISM: Artificial Sequence
<220> FEATURE:
<223> OTHER INFORMATION: Description of Artificial Sequence: Synthetic
      Monomeric photoconvertible fluorescent protein variant
      mEOS2 polypeptide

<400> SEQUENCE: 6

Met Ser Ala Ile Lys Pro Asp Met Lys Ile Lys Leu Arg Met Glu Gly
1               5                   10                  15

Asn Val Asn Gly His His Phe Val Ile Asp Gly Asp Gly Thr Gly Lys
            20                  25                  30

Pro Phe Glu Gly Lys Gln Ser Met Asp Leu Glu Val Lys Glu Gly Gly
        35                  40                  45
```

```
Pro Leu Pro Phe Ala Phe Asp Ile Leu Thr Thr Ala Phe His Tyr Gly
     50                  55                  60

Asn Arg Val Phe Ala Lys Tyr Pro Asp Asn Ile Gln Asp Tyr Phe Lys
 65                  70                  75                  80

Gln Ser Phe Pro Lys Gly Tyr Ser Trp Glu Arg Ser Leu Thr Phe Glu
                 85                  90                  95

Asp Gly Gly Ile Cys Ile Ala Arg Asn Asp Ile Thr Met Glu Gly Asp
                100                 105                 110

Thr Phe Tyr Asn Lys Val Arg Phe Tyr Gly Thr Asn Phe Pro Ala Asn
             115                 120                 125

Gly Pro Val Met Gln Lys Lys Thr Leu Lys Trp Glu Pro Ser Thr Glu
        130                 135                 140

Lys Met Tyr Val Arg Asp Gly Val Leu Thr Gly Asp Ile His Met Ala
145                 150                 155                 160

Leu Leu Glu Gly Asn Ala His Tyr Arg Cys Asp Phe Arg Thr Thr
                165                 170                 175

Tyr Lys Ala Lys Glu Lys Gly Val Lys Leu Pro Gly Tyr His Phe Val
             180                 185                 190

Asp His Cys Ile Glu Ile Leu Ser His Asp Lys Asp Tyr Asn Lys Val
             195                 200                 205

Lys Leu Tyr Glu His Ala Val Ala His Ser Gly Leu Pro Asp Asn Ala
    210                 215                 220

Arg Arg
225

<210> SEQ ID NO 7
<211> LENGTH: 225
<212> TYPE: PRT
<213> ORGANISM: Artificial Sequence
<220> FEATURE:
<223> OTHER INFORMATION: Description of Artificial Sequence: Synthetic
      Monomeric photoconvertible fluorescent protein variant
      Dendra 2 polypeptide

<400> SEQUENCE: 7

Met Asn Leu Ile Lys Glu Asp Met Arg Val Lys Val His Met Glu Gly
 1               5                  10                  15

Asn Val Asn Gly His Ala Phe Val Ile Glu Gly Glu Gly Lys Gly Lys
            20                  25                  30

Pro Tyr Glu Gly Thr Gln Thr Ala Asn Leu Thr Val Lys Glu Gly Ala
        35                  40                  45

Pro Leu Pro Phe Ser Tyr Asp Ile Leu Thr Thr Ala Val His Tyr Gly
     50                  55                  60

Asn Arg Val Phe Thr Lys Tyr Pro Glu Asp Ile Pro Asp Tyr Phe Lys
 65                  70                  75                  80

Gln Ser Phe Pro Glu Gly Tyr Ser Trp Glu Arg Thr Met Thr Phe Glu
                 85                  90                  95

Asp Lys Gly Ile Cys Thr Ile Arg Ser Asp Ile Ser Leu Glu Gly Asp
                100                 105                 110

Cys Phe Phe Gln Asn Val Arg Phe Lys Gly Thr Asn Phe Pro Pro Asn
             115                 120                 125

Gly Pro Val Met Gln Lys Lys Thr Leu Lys Trp Glu Pro Ser Thr Glu
        130                 135                 140

Lys Leu His Val Arg Asp Gly Leu Leu Val Gly Asn Ile Asn Met Ala
145                 150                 155                 160
```

```
Leu Leu Leu Glu Gly Gly Gly His Tyr Leu Cys Asp Phe Lys Thr Thr
            165                 170                 175

Tyr Lys Ala Lys Lys Val Val Gln Leu Pro Asp Ala His Phe Val Asp
            180                 185                 190

His Arg Ile Glu Ile Leu Gly Asn Asp Ser Asp Tyr Asn Lys Val Lys
            195                 200                 205

Leu Tyr Glu His Ala Val Ala Arg Tyr Ser Pro Leu Pro Ser Gln Ala
        210                 215                 220

Trp
225

<210> SEQ ID NO 8
<211> LENGTH: 225
<212> TYPE: PRT
<213> ORGANISM: Artificial Sequence
<220> FEATURE:
<223> OTHER INFORMATION: Description of Artificial Sequence: Synthetic
      Monomeric photoconvertible fluorescent protein variant
      Kaede polypeptide

<400> SEQUENCE: 8

Met Ser Leu Ile Lys Pro Glu Met Lys Ile Lys Leu Leu Met Glu Gly
1               5                   10                  15

Asn Val Asn Gly His Gln Phe Val Ile Glu Gly Asp Gly Lys Gly His
            20                  25                  30

Pro Phe Glu Gly Lys Gln Ser Met Asp Leu Val Val Lys Glu Gly Ala
        35                  40                  45

Pro Leu Pro Phe Ala Tyr Asp Ile Leu Thr Thr Ala Phe His Tyr Gly
    50                  55                  60

Asn Arg Val Phe Ala Lys Tyr Pro Asp His Ile Pro Asp Tyr Phe Lys
65                  70                  75                  80

Gln Ser Phe Pro Lys Gly Phe Ser Trp Glu Arg Ser Leu Met Phe Glu
                85                  90                  95

Asp Gly Gly Val Cys Ile Ala Thr Asn Asp Ile Thr Leu Lys Gly Asp
            100                 105                 110

Thr Phe Phe Asn Lys Val Arg Phe Asp Gly Val Asn Phe Pro Pro Asn
        115                 120                 125

Gly Pro Val Met Gln Lys Lys Thr Leu Lys Trp Glu Ala Ser Thr Glu
    130                 135                 140

Lys Met Tyr Leu Arg Asp Gly Val Leu Thr Gly Asp Ile Thr Met Ala
145                 150                 155                 160

Leu Leu Leu Lys Gly Asp Val His Tyr Arg Cys Asp Phe Arg Thr Thr
                165                 170                 175

Tyr Lys Ser Arg Gln Glu Gly Val Lys Leu Pro Gly Tyr His Phe Val
            180                 185                 190

Asp His Cys Ile Ser Ile Leu Arg His Asp Lys Asp Tyr Asn Glu Val
        195                 200                 205

Lys Leu Tyr Glu His Ala Val Ala His Ser Gly Leu Pro Asp Asn Val
    210                 215                 220

Lys
225

<210> SEQ ID NO 9
<211> LENGTH: 232
<212> TYPE: PRT
<213> ORGANISM: Artificial Sequence
<220> FEATURE:
<223> OTHER INFORMATION: Description of Artificial Sequence: Synthetic
```

Monomeric photoconvertible fluorescent protein variant
mKIKGR polypeptide

<400> SEQUENCE: 9

Met Ser Val Ile Thr Ser Glu Met Lys Ile Glu Leu Arg Met Glu Gly
1               5                   10                  15

Ser Val Asn Gly His Lys Phe Val Ile Thr Gly Lys Gly Ser Gly Arg
            20                  25                  30

Pro Tyr Glu Gly Thr Gln Thr Val Asp Leu Thr Val Ile Glu Gly Gly
        35                  40                  45

Pro Leu Pro Phe Ala Phe Asp Ile Leu Thr Thr Ala Phe His Tyr Gly
    50                  55                  60

Asn Arg Val Phe Val Glu Tyr Pro Glu Glu Ile Val Asp Tyr Phe Lys
65                  70                  75                  80

Gln Ser Phe Pro Glu Gly Tyr Ser Trp Glu Arg Ser Met Ser Tyr Glu
                85                  90                  95

Asp Gly Gly Ile Cys Leu Ala Thr Asn Asn Ile Thr Met Lys Lys Asp
            100                 105                 110

Gly Ser Asn Thr Phe Val Asn Glu Ile Arg Phe Asp Gly Thr Asn Phe
        115                 120                 125

Pro Ala Asn Gly Pro Val Met Gln Arg Lys Thr Val Lys Trp Glu Pro
    130                 135                 140

Ser Thr Glu Lys Met Tyr Val Arg Asp Gly Val Leu Lys Gly Asp Val
145                 150                 155                 160

Glu Met Ala Leu Leu Leu Glu Gly Gly Gly His Tyr Arg Cys Asp Phe
                165                 170                 175

Arg Thr Thr Tyr Lys Ala Lys Lys Val Val Gln Leu Pro Asp Tyr His
            180                 185                 190

Tyr Val Asp His Gln Met Glu Ile Thr Ser His Asp Lys Asp Tyr Asn
        195                 200                 205

Lys Val Lys Ala Tyr Glu His Ala Lys Ala Tyr Ser Gly Thr Tyr Arg
    210                 215                 220

Gly Ala Lys Tyr Glu Phe Glu Ala
225                 230

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      Clavularia cyan fluorescent protein variant mTFP1
      peptide

<400> SEQUENCE: 10

Met Val Ser Lys Gly Glu Glu
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      Clavularia cyan fluorescent protein variant mTFP1
      peptide

```
<400> SEQUENCE: 11

Gly Met Asp Glu Leu Tyr Lys
1               5
```